US010617878B2

(12) United States Patent
Fischer et al.

(10) Patent No.: US 10,617,878 B2
(45) Date of Patent: Apr. 14, 2020

(54) HEADERBLOCK WITH CERMET FEEDTHROUGH FOR AN IMPLANTABLE ELECTRICAL MEDICAL DEVICE

(71) Applicant: Heraeus Deutschland GmbH & Co. KG, Hanau (DE)

(72) Inventors: Jean-Francois Fischer, Etoy (CH); Ulrich Hausch, Frankfurt (DE); Jens Troetzschel, Ronneburg (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 223 days.

(21) Appl. No.: 15/679,716

(22) Filed: Aug. 17, 2017

(65) Prior Publication Data

US 2018/0071538 A1    Mar. 15, 2018

(30) Foreign Application Priority Data

Aug. 17, 2016 (EP) ..................................... 16184559

(51) Int. Cl.
*B32B 27/02* (2006.01)
*A61N 1/375* (2006.01)
*A61B 5/00* (2006.01)

(52) U.S. Cl.
CPC ............. *A61N 1/3754* (2013.01); *A61B 5/686* (2013.01); *A61N 1/37512* (2017.08); *A61N 1/37514* (2017.08)

(58) Field of Classification Search
CPC ................. A61B 5/686; A61N 1/37512; A61N 1/37514; A61N 1/3754
See application file for complete search history.

(56) References Cited

U.S. PATENT DOCUMENTS

| | | | |
|---|---|---|---|
| 4,934,366 | A | 6/1990 | Truex et al. |
| 7,711,427 | B2 | 5/2010 | Janzig et al. |
| 7,711,428 | B2 | 5/2010 | Janzig et al. |
| 2012/0193117 | A1 | 8/2012 | Specht et al. |
| 2012/0193141 | A1 | 8/2012 | Reisinger et al. |
| 2012/0194981 | A1 | 8/2012 | Kempf et al. |
| 2013/0338750 | A1 | 12/2013 | Eck et al. |

*Primary Examiner* — Lawrence D Ferguson
(74) *Attorney, Agent, or Firm* — Dicke, Billig & Czaja, PLLC

(57) ABSTRACT

One aspect relates to a composite including a ceramic body, including a ceramic, a first surface, and a hole, including a front face, an end face and a lateral surface. The front face is an opening in the first surface. The ceramic body further includes a second surface and conductor a1. The conductor a1 electrically connects the second surface to the lateral surface, and includes a cermet.

15 Claims, 15 Drawing Sheets

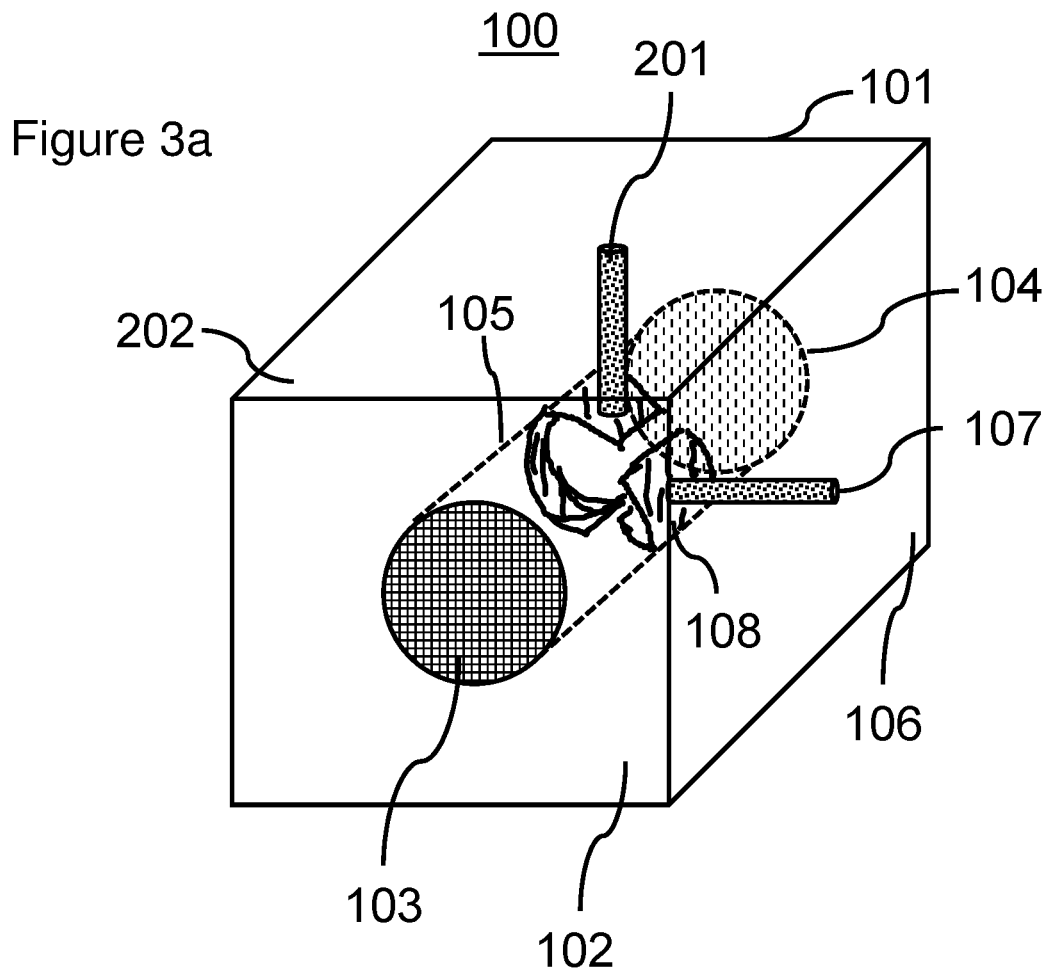
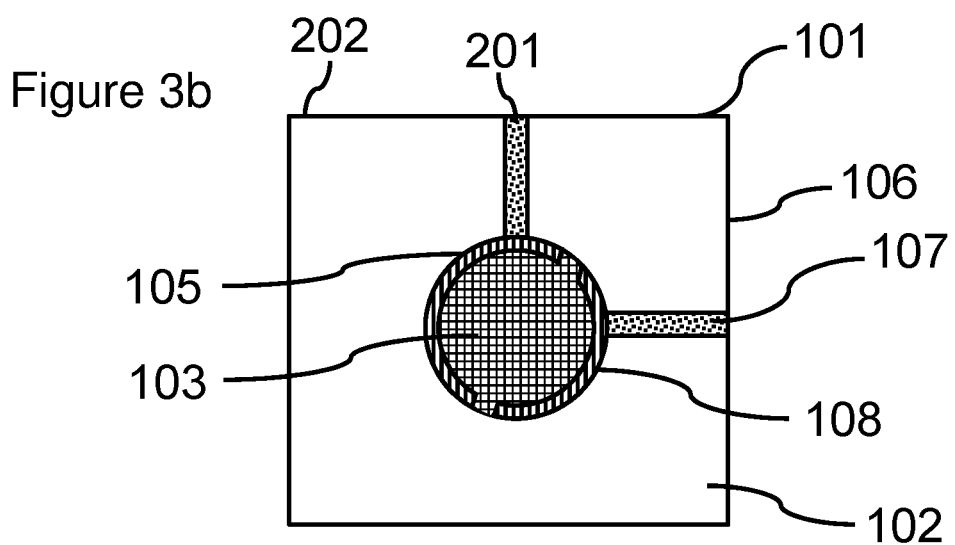

100

100

100

900

900

1200

1300

HEADERBLOCK WITH CERMET FEEDTHROUGH FOR AN IMPLANTABLE ELECTRICAL MEDICAL DEVICE

CROSS-REFERENCE TO RELATED APPLICATIONS

This Utility patent application claims priority to European Patent Application No. EP 16184559.9, filed on Aug. 17, 2016, which is incorporated herein by reference.

BACKGROUND

One embodiment relates to a composite including a ceramic body, including a ceramic; a first surface; a hole, including a front face, an end face and a lateral surface, wherein the front face is an opening in the first surface; a second surface; and a conductor a1, wherein the conductor a1 electrically connects the second surface to the lateral surface, and includes a cermet.

Furthermore, one embodiment relates to a process for producing a ceramic body including a plurality of cermet conductors; to another process for producing a ceramic body including a plurality of cermet conductors; to another process for producing a ceramic body including a plurality of cermet conductors; to yet another process for producing a ceramic body including a plurality of cermet conductors; to a composite obtainable by said processes; to a device including one of the above composites; to a use of one of the above composites to electrically connect an electrode to an implantable electrical medical device; to a process of implanting the above device into an eukaryotic organism; and to a use of the above device in a therapy.

The prior art knows numerous implantable electrical medical devices, for example pacemakers and defibrillators. Pacemakers known in the prior art comprise a bladder pacemaker, a breath pacemaker, an intestinal pacemaker, a diaphragm pacemaker, a cerebral pacemaker and a cardiac pacemaker. Such devices are commonly implanted into a human or animal body to provide a therapy or treatment for a disease or malfunction of the body. Therefore, the device is generally designed to stimulate organic tissue, for example, muscle or nerve cells, by providing electrical voltage pulses to the tissue, or to measure electrical signals of the body, or both. In each case an electrical lead which contacts patient tissue at a stimulating or measuring end is required. Remote from the stimulating or measuring end, at the other end of the lead, the connector end, the lead has to be electrically connected to the medical device. Commonly, the implantable device includes a housing which is hermetically sealed and thus leak tight with regard to body fluids and gases. This housing includes electronics and a source of electrical energy, usually a battery. The technical challenge is to electrically connect the electronics inside the hermetically sealed housing to the lead outside. In a classical arrangement this is achieved by providing an electrical feedthrough and a connector block. The electrical feedthrough includes a conductive element, usually a pin or a wire made of platinum, which extends from the inside of the housing to the outside. Therein, the conductive element is electrically insulated from the housing by an insulating body, usually a ceramic ring. Of course, the feedthrough has to be leak tight in order to keep the housing hermetically sealed. This is typically achieved by welding a titanium flange into an aperture of the housing. The ceramic ring is welded or soldered into the flange and the conductive element is soldered by a gold solder into the ceramic ring. Hence, the feedthrough provides an electrical connection between the inside of the hermetically sealed housing and the outside. In order to be able to connect the lead the connector block is applied. The connector block is electrically connected to the feedthrough at the outside of the housing. The connector block provides a single or multiple female connectors which can accommodate the connector end of one or more leads. The connector ends are usually fixed within the female connectors by screws. This setup incorporates the classical external connector block.

An improvement has been provided in the prior art by means of internal feedthrough connectors. Such internal feedthrough connectors are disclosed in U.S. Pat. Nos. 4,934,366 A, 7,711,427 B2 and 7,711,428 B2. Therein, the connector block has been incorporated into the hermetically sealed housing. Hence, the connector block and the feedthrough have been fused into one component. This further development provides advantages over the classical external arrangement with regard to miniaturising, reduction of the number of components, and reduction of labour and production time required to manufacture the implantable medical device.

However, the classical external feedthrough and connector block setup as well as the internal feedthrough connectors of the prior art include at least the following disadvantages. Both setups are characterised by a high degree of complexity. Manufacturing such a setup of the prior art takes a rather long time and a lot of labour. The setups of the prior art include a high number of parts and components which have to be assembled in a high number of process steps. This leads to rather high production costs of implantable electrical medical devices of the prior art. Furthermore, the reliability of implantable electrical medical devices directly affects the health of the patient to be treated. Hence, there is a steady need for further improvements with regard to reliability.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1b is a cross-sectional scheme of the composite according to the embodiment of FIG. 1a.

FIG. 2b is a cross-sectional scheme of the composite according to the embodiment of FIG. 2a.

FIG. 3a is a scheme in perspective of another composite according to one embodiment.

FIG. 3b is a cross-sectional scheme of the composite according to the embodiment of FIG. 3a.

FIG. 4b is a cross-sectional scheme of the composite according to the embodiment of FIG. 4a.

FIG. 14b is a cross-sectional scheme illustrating the same process as FIG. 14a.

FIG. 15b is a cross-sectional scheme illustrating the same process as FIG. 15a.

DETAILED DESCRIPTION

Figure 1A:
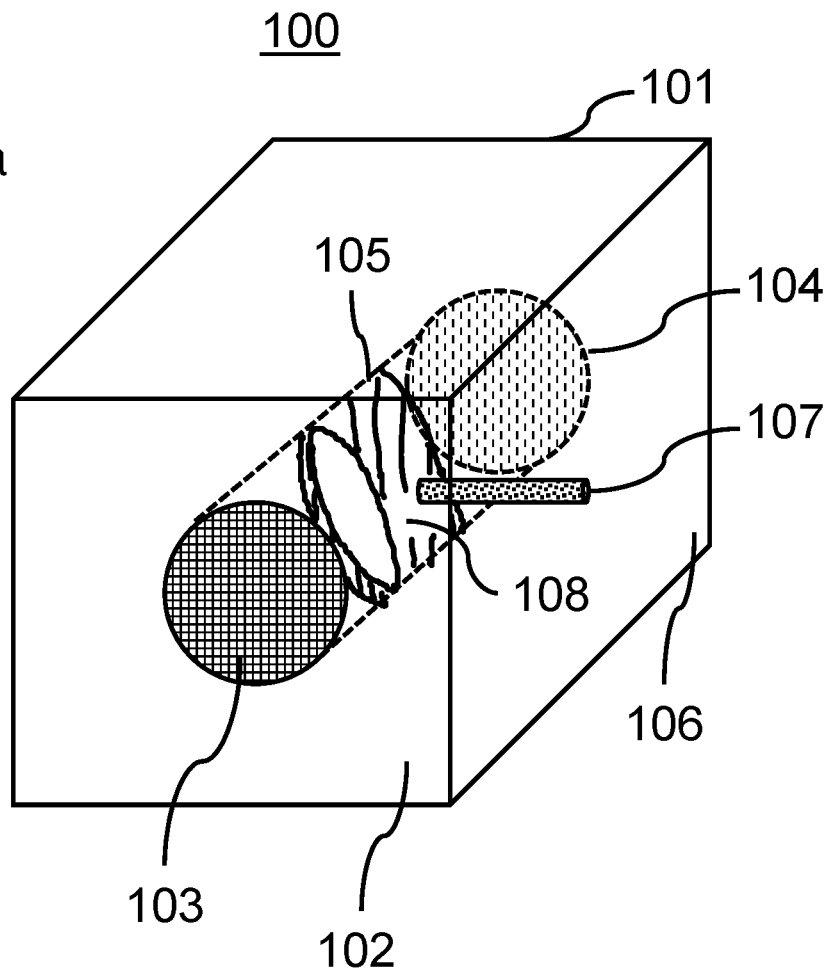
FIG. 1a is a scheme in perspective of a composite according to one embodiment.

In the following Detailed Description, reference is made to the accompanying drawings, which form a part hereof, and in which is shown by way of illustration specific embodiments in which the embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments is defined by the appended claims.

It is to be understood that the features of the various exemplary embodiments described herein may be combined with each other, unless specifically noted otherwise.

One embodiment provides an improvement of the setups of the prior art described above. Therein, the feedthrough header block (FHB) according to one embodiment incorporates one or more feedthroughs and one or more connectors. The FHB according to one embodiment may be used in an internal or external setup. This means, the FHB may be positioned inside the hermetically sealed housing of an implantable electrical medical device or outside of said housing. This provides a wide range of flexibility and options to combine the FHB of one embodiment with medical devices available in the prior art.

One embodiment at least partly overcome a disadvantage arising from the prior art. One embodiment provides a FHB for an implantable electrical medical device, wherein the FHB is characterized by a reduced number of components. One embodiment provides a FHB for an implantable electrical medical device, wherein the FHB is less complicated or less costly or both to produce. One embodiment provides a FHB for a medical implantable electrical device, wherein the FHB has a more simple design. One embodiment provides a FHB for an implantable electrical medical device, wherein the FHB includes less brazings. One embodiment provides a FHB for an implantable electrical medical device, wherein the FHB allows for a higher number of lead connections. One embodiment provides a FHB for an implantable electrical medical device, wherein the FHB can be used internally and externally to a housing of the implantable electrical medical device. One embodiment provides a FHB for an implantable electrical medical device, wherein the FHB allows multiple electrical connections around a circumference of a connector end of a lead or around a female connector of the FHB or both. One embodiment provides a FHB for an implantable electrical medical device, wherein the FHB allows an increased electrical connection density of a lead at the connector end of the lead. One embodiment provides a FHB for an implantable electrical medical device, wherein the FHB is suitable for connecting a deep brain stimulation electrode to the implantable electrical medical device.

One embodiment provides a FHB for an implantable electrical medical device, wherein the FHB includes a cermet feedthrough, wherein the FHB is characterized by at least one of the above advantages. One embodiment provides an implantable electrical medical device including an FHB, wherein the FHB is characterized by at least one of the above advantages. One embodiment provides an implantable pacemaker, a biomonitor or an implantable neuro stimulator or recorder, or any other implantable device requiring a detachable lead, each including an FHB, wherein the FHB is characterized by at least one of the above advantages. One embodiment provides a medical implantable electrical device component which is characterized by a longer durability period in a body. One embodiment provides a medical implantable electrical device component which is less prone to defects when being used in a body. One embodiment provides a medical implantable electrical device component which works more reliable when implanted in a body. One embodiment provides a medical implantable electrical device component which is less complicated or less expensive or both to produce. One embodiment provides a pacemaker component or a biomonitor component or both which is characterized by at least one of the above advantages of a medical implantable electrical device.

One embodiment provides a process for the production of a FHB, wherein the process includes less process steps. One embodiment provides a process for the production of a FHB, wherein the process is less complicated. One embodiment provides a process for the production of a FHB, wherein the process requires less manual labor. One embodiment provides a process for the production of a FHB, wherein the process takes less time or is less expensive or both.

A contribution to the solution of at least one of the above is made by an embodiment 1 of a composite 1 including a ceramic body, including a) a ceramic;
b) a first surface;
c) a hole, including a front face, an end face and a lateral surface,
  wherein the front face is an opening in the first surface;
d) a second surface; and
e) a conductor a1, wherein the conductor a1
  i) electrically connects the second surface to the lateral surface, and
  ii) includes a cermet.

In an embodiment 2 of the composite 1 the composite is designed according to its embodiment 1, wherein the composite includes at least one further conductor a2, wherein each further conductor a2
  i) electrically connects the second surface to the lateral surface, and
  ii) includes a cermet.

In an embodiment 3 of the composite 1 the composite is designed according to its embodiment 1 or 2, wherein the composite includes a third surface and at least one further conductor b2,
wherein each further conductor b2
  i) electrically connects the third surface to the lateral surface, and
  ii) includes a cermet.

In an embodiment 4 of the composite 1 the composite is designed according to its embodiment 2 or 3, wherein the conductor a1 connects the second surface to a first circumferential position on the lateral surface, wherein the at least one further conductor a2 or the at least one further conductor b2 or both connects the second surface or the third surface or both to a further circumferential position on the lateral surface, wherein the first circumferential position has a distance from the further circumferential position along a circumference of the lateral surface, wherein the distance is at least $\frac{1}{360}^{th}$, in one embodiment at least $\frac{1}{72}^{nd}$, more in one embodiment at least $\frac{1}{4}^{th}$, and in one embodiment at least $\frac{1}{3}^{rd}$, of the circumference. This means that the first circumferential position is spaced from the further circumferential position along the circumference of the lateral surface by at least 1°, in one embodiment at least 5°, in one embodiment at least 90°, in one embodiment at least 120°, along the circumference of the lateral surface, wherein the circumference goes 360° around the lateral surface. In one embodiment, the conductor a1, the further conductors a2 and the further conductors b2 connect to circumferential positions on the circumference of the lateral surface which are equidistantly distributed along the circumference of the lateral surface.

In an embodiment 5 of the composite 1 the composite is designed according to any of its preceding embodiments, wherein the ceramic body and the conductor a1 are in one piece.

In an embodiment 6 of the composite 1 the composite is designed according to any of its preceding embodiments, wherein the hole is designed to accommodate an electrically conductive element. In one embodiment, the hole includes an electrically conductive element. In one embodiment, each of the group consisting of the conductor a1, the further conductors a2 and the further conductors b2 connects to a separate electrically conductive element in the hole. In one embodiment, the hole is designed as a female connector. In one embodiment, a female connector is designed to accommodate a male plug end of a lead.

A contribution to the solution of at least one of the above is made by an embodiment 1 of a process 1 including as process steps
  a) providing a ceramic green body and a cermet precursor composition, wherein the ceramic green body includes a plurality of channels, wherein each channel of the plurality of channels is oriented in the ceramic body such that each channel of the plurality of channels can be connected to the other channels of the plurality of channels by providing exactly one hole extending through the ceramic green body;
  b) filling the channels with the cermet precursor composition; and
  c) firing the ceramic green body and the cermet precursor composition, thereby obtaining a ceramic body including a plurality of cermet conductors.

The exactly one hole mentioned in process step a) which could connect each channel of the plurality of channels to the other channels is only imaginary. It is not necessary to really provide this hole. The hole is used here only as a means to explain the arrangement of the channels. Said hole is straight or cylindrical, or both. The channels are arranged in parallel to each other or in a star-like configuration. In case of a star-like configuration the centre of the star would be the imaginary hole. However, the channels may also mutually incline an angle, but in one embodiment, the channels do not touch each other.

In an embodiment 2 of the process 1 the process is designed according to the embodiment 1, wherein the cermet precursor composition is a cermet powder or a cermet paste or both.

A contribution to the solution of at least one of the above is made by an embodiment 1 of a process 2 including as process steps,
  a) providing a ceramic green body and a plurality of cermet conductors, wherein the ceramic green body includes a plurality of channels, wherein each channel of the plurality of channels is oriented in the ceramic body such that each channel of the plurality of channels can be connected to the other channels of the plurality of channels by providing exactly one hole extending through the ceramic green body;
  b) positioning one cermet conductor of the plurality of cermet conductors in each channel of the plurality of channels; and
  c) firing the ceramic green body and the plurality of cermet conducts, thereby obtaining a ceramic body including the plurality of cermet conductors.

The exactly one hole mentioned in process step a) which could connect each channel of the plurality of channels to the other channels is only imaginary. It is not necessary to really provide this hole. The hole is used here only as a means to explain the arrangement of the channels. Said hole is straight or cylindrical, or both. The channels are arranged in parallel to each other or in a star-like configuration. In case of a star-like configuration the centre of the star would be the imaginary hole. However, the channels may also mutually incline an angle, but in one embodiment, the channels do not touch each other.

In an embodiment 3 of the process 1, and in an embodiment 2 of the process 2 the process is designed according to anyone of its preceding embodiments, wherein in process step a) the ceramic green body includes the hole. Here, the hole which was mentioned before as an imaginary means to describe the arrangement of the channels is really provided in the ceramic green body. Therein, the hole may be provided inherently during manufacturing the ceramic green body. For example, the ceramic green body may be manufactured by pressing ceramic powder in a mould. The shape of said mould may include the hole or the mould may include an insert which provides the hole. Another means of providing the hole is drilling the hole in the pre-prepared ceramic green body. In one embodiment, drilling is a drilling by one selected from the group consisting of a laser, a jet, a water jet, and a drill or a combination of at least two thereof.

In an embodiment 4 of the process 1 the process is designed according to the embodiment 1 or 2, and in an embodiment 3 of the process 2 the process is designed according to the embodiment 1, wherein after process step c) the hole is provided in the ceramic body, including a first surface and a second surface; wherein the hole includes a front face, an end face and a lateral surface; wherein the front face is an opening in the first surface; wherein each cermet conductor of the plurality of cermet conductors electrically connects the second surface to the lateral surface. In one embodiment, the hole is provided by drilling. In one embodiment, drilling is a drilling by one selected from the group consisting of a laser, a jet, a water jet, and a drill or a combination of at least two thereof.

A contribution to the solution of at least one of the above is made by an embodiment 1 of a process 3 including as process steps
 a) providing a plurality of ceramic green sheets,
   wherein each ceramic green sheet includes a first sheet surface and a further sheet surface,
   wherein at least two of the ceramic green sheets each include a first hole,
   wherein the first hole of each of the at least two ceramic green sheets connects the first sheet surface to the further sheet surface of the ceramic green sheet,
   wherein each first hole is filled with a quantity of a cermet precursor composition;
 b) contacting the first sheet surface or the further sheet surface or both of each ceramic green sheet with the first sheet surface or the further sheet surface of another ceramic green sheet of the plurality of ceramic green sheets such that the quantities of the cermet precursor composition form a continuous path of the cermet precursor composition; and
 c) firing the plurality of ceramic green sheets and the cermet precursor composition, thereby obtaining a ceramic body including a cermet conductor.

In an embodiment 2 of the process 3 the process is designed according to embodiment 1, wherein in process step a) at least two of the ceramic green sheets each include n further holes; wherein each further hole connects the first sheet surface to the further sheet surface of the ceramic green sheet, including said further hole; wherein each further hole is filled with a further quantity of the cermet precursor composition; wherein in process step b) the first sheet surface or the further sheet surface or both of each ceramic green sheet is contacted with the first sheet surface or the further sheet surface of another ceramic green sheet of the plurality of ceramic green sheets such that the further quantities of the cermet precursor composition form n continuous paths of the cermet precursor composition; wherein in process step c) the ceramic body includes n further cermet conductors; wherein n is an integer which is at least 1, in one embodiment at least 2, in one embodiment at least 3, in one embodiment at least 5, in one embodiment at least 10, in one embodiment at least 20.

In an embodiment 3 of the process 3 the process is designed according to embodiment 1 or 2, wherein prior to process step a) each first hole is filled with a quantity of the cermet precursor composition by
 a) providing one plurality of portions of the cermet precursor composition for each first hole,
   wherein each plurality of portions of the cermet precursor composition has a first cermet precursor composition volume,
   wherein each first cermet precursor composition volume is higher than a first hole volume of a corresponding first hole;
 b) filling each plurality of portions of the cermet precursor composition into the corresponding first hole in subsequent fill-in steps,
wherein after each fill-in step a filled in portion of the cermet precursor composition is dried. In one embodiment, the portions of the plurality of portions of the cermet precursor composition are filled in portion by portion. This mean a portion is filled in and dried and subsequently a next portion is filled in and dried until all the portions are filled in and dried.

In an embodiment 4 of the process 3 the process is designed according to embodiment 2 or 3, wherein prior to process step a) each further hole is filled with a quantity of the cermet precursor composition by
 a) providing one plurality of portions of the cermet precursor composition for each further hole,
   wherein each plurality of portions of the cermet precursor composition has a further cermet precursor composition volume,
   wherein each further cermet precursor composition volume is higher than a further hole volume of a corresponding further hole;
 b) filling each plurality of portions of the cermet precursor composition into the corresponding further hole in subsequent fill-in steps,
wherein after each fill-in step a filled in portion of the cermet precursor composition is dried. In one embodiment, the portions of the plurality of portions of the cermet precursor composition are filled in portion by portion. This mean a portion is filled in and dried and subsequently a next portion is filled in and dried until all the portions are filled in and dried.

In an embodiment 5 of the process 3 the process is designed according to any of the embodiments 1 to 4, wherein the contacting of the first sheet surface or the further sheet surface or both of each ceramic green sheet with the first sheet surface or the further sheet surface of another ceramic green sheet of the plurality of ceramic green sheets is a laminating.

In an embodiment 6 of the process 3 the process is designed according to any of the embodiments 3 to 5, wherein the filling is one selected from the group consisting of a printing, an injecting, and a depositing, or a combination of at least two thereof. In one embodiment, printing is a screen printing or a stencil printing or both. In one embodiment, depositing is a physical depositing or a chemical depositing or both. In one embodiment, physical depositing is a physical vapour depositing. In one embodiment, chemical depositing is a chemical vapour depositing.

In an embodiment 7 of the process 3 the process is designed according to any of the embodiments 3 to 6, wherein during at least one of the fillings into one of the first holes a vacuum is present in the first hole. Therein, a vacuum includes a pressure which is at least 10%, in one embodiment at least 15%, in one embodiment at least 20%, in one embodiment at least 30%, in one embodiment at least 40%, in one embodiment at least 50%, in one embodiment at least 60%, lower than the pressure of the ambient air outside of the first hole, based on the ambient air pressure outside of the first hole.

In an embodiment 8 of the process 3 the process is designed according to any of the embodiments 4 to 7, wherein during at least one of the fillings into one of the further holes a vacuum is present in the further hole. Therein, a vacuum includes a pressure which is at least 10%, in one embodiment at least 15%, in one embodiment at least 20%, in one embodiment at least 30%, in one embodiment at least 40%, in one embodiment at least 50%, in one embodiment at least 60%, lower than the pressure of the ambient air outside of the further hole, based on the ambient air pressure outside of the further hole.

In an embodiment 9 of the process 3 the process is designed according to any of the embodiments 1 to 8, wherein the contacting of the first sheet surface or the further sheet surface or both of each ceramic green sheet with the first sheet surface or the further sheet surface of another ceramic green sheet of the plurality of ceramic green sheets includes a pressing by applying a pressure in the range from 100 to 500 bar, in the range from 150 to 450 bar, in one embodiment in the range from 200 to 400 bar, in one embodiment in the range from 300 to 400 bar.

In an embodiment 10 of the process 3 the process is designed according to any of the embodiments 1 to 9, wherein after firing a hole is provided in the ceramic body, wherein the hole includes a front face, an end face and a lateral surface, connecting the front face to the end face, wherein the front face is an opening in the ceramic body, wherein at least one cermet conductor, all cermet conductors, touches the lateral surface. In one embodiment, the hole is provided by drilling. In one embodiment, drilling is a drilling by one selected from the group consisting of, a laser, a jet, a water jet, and a drill or a combination of at least two thereof.

In an embodiment 5 of the process 1 the process is designed according to its embodiment 1 or 2, and in an embodiment 11 of the process 3 the process is designed according to any of its embodiments 1 to 10, wherein the cermet precursor composition includes
   a) Pt in the range from 60 wt.-% to the remainder completing the sum of all components to 100 wt.-%, in the range from 65 wt.-% to the remainder completing the sum of all components to 100 wt.-%, in one embodiment in the range from 70 wt.-% to the remainder completing the sum of all components to 100 wt.-%, in one embodiment in the range from 80 wt.-% to the remainder completing the sum of all components to 100 wt.-%,
   b) $Al_2O_3$ in the range from 0.5 to 25 wt.-%, in the range from 0.5 to 20 wt.-%, in one embodiment in the range from 1 to 15 wt.-%, in one embodiment in the range from 1.1 to 8 wt.-%, in one embodiment in the range from 1.7 to 4.5 wt.-%,
   c) a vehicle in the range from 8 to 30 wt.-%, in the range from 9 to 28 wt.-%, in one embodiment in the range from 9 to 22 wt.-%, in one embodiment in the range from 9 to 12 wt.-%, 9 to 14 wt %,
each based on the total weight of the cermet precursor composition.

A contribution to the solution of at least one of the above is made by an embodiment 1 of a composite 2 obtainable by the process 1 according to any of its embodiment 1 to 5, or by the process 2 according to any of its embodiments 1 to 3, or by the process 3 according to any of its embodiments 1 to 11.

A contribution to the solution of at least one of the above is made by an embodiment 1 of a device 1 including a housing, an inner volume, an outer volume, and the composite 1 according to any of its embodiments 1 to 6, or the composite 2 according to its embodiment 1;
   wherein the housing
   a) encloses the inner volume,
   b) separates the inner volume from the outer volume, and
   c) includes an aperture;
wherein the aperture frames the composite.

In one embodiment, a device is an electrical device. In one embodiment, an electrical device is an implantable electrical device. In one embodiment, an implantable electrical device is a medical implantable electrical device. In one embodiment, an medical implantable electrical device is one selected from the group consisting of a pacemaker, a defibrillator, that is, an ICD, a cardiac resynchronisation therapy device with pacemaker function (CRT-P) or with defibrillator function (CRT-D), a cardiac monitor, a deep brain stimulator, a neuro stimulator, a vagus nerve stimulator, a spinal cord stimulator, a sacral nerve stimulator, a gastric nerve stimulator, a Cochlear implant and an implantable drug pump or a combination of at least two thereof. In one embodiment, the conductor a1 electrically connects the inner volume to the outer volume. In one embodiment, the conductor a1 and each further conductor a2 and b2 electrically connect the inner volume to the outer volume. In one embodiment, the device is a biomonitor. In one embodiment, the housing hermetically seals the inner volume from the outer volume.

In an embodiment 2 of the device 1 the device is designed according to its embodiment 1, wherein the inner volume includes one selected from the group consisting of the hole, the conductor a1, each further conductor a2, and each further conductor b2, or a combination of at least two thereof. In this embodiment, the composite is used in an internal arrangement with respect to the housing.

In an embodiment 3 of the device 1 the device is designed according to its embodiment 1 or 2, wherein the outer volume includes one selected from the group consisting of the hole, the conductor a1, each further conductor a2, and each further conductor b2, or a combination of at least two thereof. In this embodiment the composite is used in an external arrangement with respect to the housing.

In an embodiment 4 of the device 1 the device is designed according to any of its embodiments 1 to 3, wherein the device is an implantable electrical medical device. In one embodiment, an implantable electrical medical device is one selected from the group consisting of a pacemaker, a neurostimulator, a measuring device and a defibrillator or a combination of at least two thereof. In one embodiment, a pacemaker is one selected from the group consisting of a bladder pacemaker, a breath pacemaker, an intestinal pacemaker, a diaphragm pacemaker, a cerebral pacemaker and a cardiac pacemaker or a combination of at least two thereof. In one embodiment, a pacemaker is a cardiac pacemaker. In one embodiment, a measuring device is a biomonitor.

A contribution to the solution of at least one of the above is made by an embodiment 1 of a use 1 of the composite 1 according to any of its embodiments 1 to 6, or the composite 2 according to its embodiment 1 to electrically connect an electrode to an implantable electrical medical device.

A contribution to the solution of at least one of the above is made by an embodiment 1 of a process 4 including as process steps
   a) providing the device 1 according to any of its embodiments 1 to 4; and
   b) implanting the device into an eukaryotic organism.

A contribution to the solution of at least one of the above is made by an embodiment 1 of a use 2 of the device 1 according to any of its embodiments 1 to 4 in a therapy. In one embodiment, a therapy is a therapy of one selected from the group consisting of bradycardia, heart block, ventricular fibrillation, ventricular tachycardia, a chronic heart failure, heart failure induced conduction disturbances, ventricular dyssynchrony, atrial fibrillation, Alzheimer's disease, Parkinson's disease, a tremor, a depression, epilepsy, surdity, dystonia, obsessive-compulsive disorder, Tourette syndrome, a trauma, a coma, chronic back pain, failed back surgery syndrome, complex regional pain syndrome, refractory pain due to ischemia, urinary urge incontinence, urinary retention, urinary frequency, fecal incontinence, idiopathic constipation, interstitial cystitis, chronic anal fissure, obesity and a chronic pain or a combination of at least two thereof.

Hole

For the use throughout this document a hole is to be understood as a channel-like or tunnel-like cavity. Said cavity may extend into the volume or material including the hole, but not through the volume or material. Such hole is referred to as a blind-hole throughout this text. Each hole includes a front face, an end face and a lateral surface. The lateral surface connects the front face to the end face. Therein, the lateral surface is a material surface within the ceramic body. The front face is not a material surface. The front face is rather a geometric surface only as the front face is an opening in the first surface of the ceramic body. The end face may be a material surface or a geometric surface or both. The hole may be a through-hole in the ceramic body. In this case the front face is an opening of the ceramic body, an "entrance", and the end face is another opening in the ceramic body, an "exit". Here the end face is not a material surface. Only the lateral surface which provides the tunnel or channel between the front face and the end face is a material surface. In another case, the hole is a blind-hole. Here the front face is again an opening in the ceramic body, hence a non-material surface. The end face is positioned within the ceramic body and represents a material surface of the ceramic body. There is an "entrance", but no "exit". Therein, in any case the front face and the end face and a transversal cross section of the lateral surface of the hole can have any shape of a geometrical surface that seems applicable according to one embodiment to the skilled person. Therein, the front face, the end face and the cross section of the lateral surface have to be shaped to be able to accommodate a male connector end of a lead. In one embodiment, a front face is cyclic or rectangular or both. In one embodiment, an end face is cyclic or rectangular or both. In one embodiment, a lateral surface of the hole is at least partly cylindrical. In one embodiment, a lateral surface of the hole is prism-shaped or tortuous or both.

In one embodiment, a ceramic body includes at least two, in one embodiment, an at least three, in one embodiment, an at least four, in one embodiment at least five, in one embodiment at least 10, in one embodiment at least 20, holes as described above. Therein, each hole is electrically connected by one or more conductors as described in the context of one embodiment.

Ceramic

A ceramic according to one embodiment can be any ceramic the skilled person deems applicable to the embodiment. In one embodiment ceramic is electrically insulating. In one embodiment, the ceramic is selected from the group consisting of an oxide ceramic, a silicate ceramic and a non-oxide ceramic or a combination of at least two thereof.

The oxide ceramic includes a metal oxide or a metalloid oxide or both. In one embodiment, a metal of the metal oxide is selected from the group consisting of aluminium, zirconium, titanium, or a combination of at least two thereof. In one embodiment metal oxide is selected from the group consisting of aluminium oxide ($Al_2O_3$); magnesium oxide (MgO); zirconium oxide ($ZrO_2$); yttrium oxide ($Y_2O_3$); aluminium titanate ($Al_2TiO_5$); a piezo ceramic as for example lead-zirconate ($PbZrO_3$), lead-titanate ($PbTiO_3$) and lead-circonate-titanate (PZT); or a combination of at least two thereof. In one embodiment metalloid of the metalloid oxide is selected from the group consisting of boron, silicon, tellurium, or a combination of at least two thereof. In one embodiment oxide ceramic includes one selected from the group consisting of aluminium oxide toughened with zirconium oxide enhanced (ZTA—Zirconia Toughened Aluminium—$Al_2O_3/ZrO_2$), zirconium oxide toughened with yttrium (Y-TZP), barium (Zr, Ti)oxide, barium (Ce, Ti)oxide or a combination of at least two thereof.

In one embodiment, the silicate ceramic is selected from the group consisting of a steatite ($Mg_3[Si_4O_{10}(OH)_2]$), a cordierite (Mg, $Fe^{2+})_2(Al_2Si)[Al_2Si_4O_{18}]$), a mullite ($Al_2Al_{2+2x}Si_{2-2x}O_{10-x}$ with x=oxide defects per unit cell), a feldspar $(Ba,Ca,Na,K,NH_4)(Al,B,Si)_4O_8)$ or a combination of at least two thereof.

In one embodiment, the non-oxide ceramic includes a carbide or a nitride or both. In one embodiment, carbide is one selected from the group consisting of silicon carbide (SiC), boron carbide ($B_4C$), titanium carbide (TiC), tungsten carbide, cementite ($Fe_3C$) or a combination of at least two thereof. In one embodiment, nitride is one selected from the group consisting of silicon nitride ($Si_3N_4$), aluminium nitride (AlN), titanium nitride (TiN), silicon aluminium oxinitride (SIALON) or a combination of at least two thereof. In one embodiment, non-oxide ceramic is sodium-potassium-niobate.

For the use throughout this document a ceramic precursor composition is a composition from which by firing a ceramic can be obtained. In one embodiment, ceramic precursor composition is a ceramic powder or a ceramic paste or both. In one embodiment, ceramic paste includes a ceramic powder and a vehicle. In one embodiment, vehicle is an organic vehicle. The amount of vehicle in the paste is chosen in order to obtain an optimal viscosity of the paste. For the use throughout this document a ceramic green sheet is a ceramic precursor sheet, wherein by firing the ceramic precursor sheet a ceramic sheet can be prepared. For the use throughout this document a ceramic green body is a ceramic precursor body, wherein by firing the ceramic precursor body a ceramic body can be prepared.

Cermet

According to one embodiment a cermet is a composite material, including at least one ceramic component in at least one metallic p or a composite material, including at least one metallic component in a least one ceramic matrix; or both. At least one ceramic powder and at least one metallic powder can for example be applied for preparing a cermet, wherein to at least one of the powders for example a binder can be added and optionally at least one surfactant. In one embodiment, the ceramic powder/the ceramic powders of the cermet have a median grain size of less than 10 µm, in one embodiment less than 5 µm, in one embodiment less than 3 µm. In some cases the ceramic powder of the cermet has an average particle size of at least 15 µm. In one embodiment, the metallic powder/the metallic powders of the cermet have an average grain size of less than 15 µm, in one embodiment less than 10 µm, in one embodiment less than 5 µm. Therein, the average grain size is the median value or the $D_{50}$. The $D_{50}$ gives the value, at which 50% of the grains of the ceramic powder and/or the metallic powder are smaller than the $D_{50}$. In one embodiment, a cermet is characterised by a high specific conductivity, which is at least 1 S/m, in one embodiment at least $10^3$ S/m, in one embodiment at least $10^4$ S/m. The at least one ceramic component of the cermet according to one embodiment includes a ceramic according to one embodiment. The at least one metallic component of the cermet according to one embodiment includes one selected from the group consisting of platinum, iridium, niobium, palladium, iron, stainless steel, a cobalt-chromium-alloy, molybdenum, tantalum, tungsten, titanium, cobalt and zirconium and gold or a combination of at least two thereof. Therein a combination is an alloy. In one embodiment, stainless steel is stainless steel 316L. Generally, the cermet becomes electrically conductive if the metal content of the cermet is above the so called percolation threshold, at which metal particles in the sintered cermet are at least partly connected to each other in such a way that electrical charges can be transported via conduction. Therefore, the metal content of the cermet should according to experience depending on the choice of materials be at least 25 vol.-%, in one embodiment at least 32 vol.-%, in one embodiment at least 38 vol.-%, each based on the total volume of the cermet.

For the use throughout this document a cermet precursor composition is a composition from which by firing a cermet can be obtained. In one embodiment cermet precursor composition is a cermet powder or a cermet paste or both. In one embodiment, cermet paste includes a cermet powder and a vehicle. In one embodiment, vehicle is an organic vehicle. The amount of vehicle in the paste is chosen in order to obtain an optimal viscosity of the paste.

Ceramic Body

A ceramic body is a geometric body made of a ceramic. Therein, a geometric body may have any geometric shape the skilled person deems appropriate for a FHB. For example, the ceramic body may be of the shape of a rectangular block or box-shaped or both. If the ceramic body is used in an external setup, this means the ceramic body is positioned outside of a housing of an implantable electrical medical device, corners and edges of the ceramic body are rounded in order to prevent injuring the patient's body when being implanted. In one embodiment, the ceramic body is cylindrically shaped. A wide variety of geometric shapes which are suitable for implantable medical devices are known in the prior art. For example, in one embodiment a shape should allow the implantable medical device, in which the composite having the ceramic body may be used, to be as small as possible and the shape should not cause any injuries to the host body.

Surfaces

In one embodiment, a second surface is adjacent to the first surface. In case of a cylindrically shaped ceramic body, a first surface is a front surface of the cylindrically shaped ceramic body. In case of a cylindrically shaped ceramic body, a second surface is a lateral surface of the cylindrically shaped ceramic body. In case of a box-shaped ceramic body, a first surface is a rectangular surface of the box. In case of a box-shaped ceramic body, a second surface is a rectangular surface of the box. In one embodiment, a third surface is opposite to the second surface.

Drying

In one embodiment, drying includes a peak temperature in the range from 50 to 500° C., in one embodiment in the range from 70 to 400° C., in one embodiment in the range from 100 to 300° C., in one embodiment in the range from 100 to 200° C. In one embodiment, drying is performed for at least 3 minutes, in one embodiment for at least 4 minutes, in one embodiment for at least 5 minutes, in one embodiment for at least 7 minutes, in one embodiment for at least 10 minutes.

Firing

Firing can be performed in any oven the skilled person deems appropriate for firing the respective green sheet. In one embodiment, firing is performed in a box oven. In one embodiment, firing includes a peak temperature in the range from 1000 to 2000° C., in one embodiment in the range from 1250 to 1900° C., in one embodiment in the range from 1510 to 1650° C. In one embodiment, firing includes keeping a peak temperature constant for a duration in the range from 0.3 to 10 hours, in one embodiment in the range from 0.5 to 7 hours, in one embodiment in the range from 1 to 5 hours.

Conductor

The conductor a1 and the at least one further conductor a2 provide electrical connections between the second surface and the lateral surface of the hole. The at least one further conductor b2 provides electrical connection between the third surface and the lateral surface of the hole. Therein, the electrical connections are provided by the cermet included by the respective conductor. In one embodiment, a conductor has a channel-like or tunnel-like shape. Therein, the channel or tunnel is filled with the cermet. The channel or tunnel may be straight or curved. In one embodiment, a channel or tunnel is straight or straight with a linkage. A transversal cross section of the conductor may have any geometric shape the skilled person deems appropriate. In one embodiment, a conductor is at least partly cylindrically shaped. In one embodiment, a conductor consists of a rod made of the cermet. In one embodiment, a conductor consists of two or more rods each made of the cermet and each rod at one end being in contact with an end of another rod, wherein the rods incline an angle. In one embodiment, the ceramic body and at least one selected from the group consisting of the conductor a1, the at least one further conductor a21 and the at least one further conductor b2 or a combination of at least two thereof, all such conductors, are in one piece. This means, the ceramic body and the respective conductor are fired together to form a single body without brazings or other intermaterial connections.

Electrically Conductive Element

In one embodiment, the hole in the ceramic body is designed to accommodate an electrically conductive element. In one embodiment, an electrically conductive element is one selected from the group consisting of a lead, a plug, a pin and a mechanical adjustment element or a combination of at least two thereof. In one embodiment, a mechanical adjustment element is a spring.

Eukaryotic Organism

In one embodiment, a eukaryotic organism is a body of a human being or an animal.

In one embodiment, the housing hermetically seals the inner volume from the outer volume. In the context of one embodiment the term "hermetically sealed" should mean that assuming normal operation no or only a minimum of moisture or gases may be exchanged between the inner volume and the outer volume within common durations of operation (for example 5 to 10 years). A quantity which may describe for example a permeation of gases or moisture or both through the housing is the so called leak rate. The leak rate may be measured in a leak test. A leak test may be performed using a helium leak tester and/or a mass spectrometer. Such a leak test is standardised in Mil-STD-883G method 1014. Therein, a maximum tolerable helium leak rate is determined depending on an internal volume of the device to be tested, here the inner volume. According to the methods specified in paragraph 3.1 of MIL-STD-883G, method 1014, and considering the relevant volumina and cavities of the devices to be tested in the context of one embodiment the maximum tolerable helium leak rates could for example be in the range from $1 \times 10^{-8}$ atm×cm$^3$/s to $1 \times 10^{-7}$ atm×cm$^3$/s. In the context of one embodiment the term "hermetically sealed" may, for example, mean that the housing illustrates a helium leak rate of less than $1 \times 10^{-7}$ atm×cm³/s. In one embodiment the helium leak rate may be less than 1×10⁻⁸ atm×cm³/s, in one embodiment, less than 1×10⁻⁹ atm×cm³/s.

In terms of standardising, the helium leak rates may be converted into the equivalent standard air leak rates. The definition of the equivalent standard air leak rate and the method of conversion are given in the standard ISO 3530. An implantable medical device is usually used within a human or animal body. Therefore, leak tightness and biocompatibility are commonly the main requirements that the device has to match. Implanted in a human or animal body the device usually is exposed to a fluid of a tissue of the body. Therefore, it is usually important that neither a body fluid penetrates into the housing of the device nor a fluid penetrates out of the housing. In order to ensure this, the housing should be as impenetrable as possible, for example, with regard to body fluids.

Test Methods

The following test methods are used in one embodiment. In absence of a test method, the ISO test method for the feature to be measured being closest to the earliest filing date of the present application applies. In absence of distinct measuring conditions, standard ambient temperature and pressure (SATP) as a temperature of 298.15 K (25° C., 77° F.) and an absolute pressure of 100 kPa (14.504 psi, 0.986 atm) apply.

Volume of Holes

The volume of the hole is determined geometrically as the product of the layer thickness and the area of the hole opening. Therein, the area is determined as $\pi \cdot d^2/4$ for a circular hole opening, wherein d is the diameter of the hole opening. d can be measured using an optical microscope.

Volume of Cermet Precursor Composition

The volume of the wet cermet precursor composition applied to a hole is determined as the sum of the volume of the screen aperture or stencil aperture used to apply the composition by screen or stencil printing and the volume of the hole. Therein, the volume of the aperture of the screen is determined geometrically. The volume of the screen or stencil aperture is the product of the thickness of the screen or stencil and the area of the aperture. Therein, the area is determined as $\pi \cdot d^2/4$ for a circular aperture, wherein d is the diameter of the aperture. d can be measured using an optical microscope.

Viscosity

Viscosity measurements were performed using the Thermo Fischer Scientific Corp. "Haake Rheostress 6000" equipped with a ground plate MPC60 Ti and a cone plate C 20/0.5° Ti and software "Haake RheoWin Job Manager 4.00.0007". After setting the distance zero point, a paste sample sufficient for the measurement was placed on the ground plate. The cone was moved into the measurement positions with a gap distance of 0.049 mm and excess material was removed using a spatula. The sample was equilibrated to 25° C. for three minutes and the rotational measurement started. The shear rate was increased from 0 to 15 s⁻¹ within 60 s and 30 equidistant measuring points. After a waiting time of 60 s at a shear rate of 15 s⁻¹, the shear rate was reduced from 15 to 0 s⁻¹ within 60 s and 30 equidistant measuring points. The micro torque correction, micro stress control and mass inertia correction were activated. The viscosity is given as the measured value at a shear rate of 5 s⁻¹ of the downward shear ramp.

Scanning Electron Microscopy (SEM)

The sample is cut in a way that the area of interest is laid open. In this case perpendicular to the surface of the substrate so that a cross section of the different layers was obtained. The cut sample is placed in a container filled with embedding material and oriented such that the area of interest is on top. As embedding material, EpoFix (Struers GmbH) is used, mixed according to the instructions. After 8 hours curing at room temperature the sample can be processed further. In a first step the sample is ground with a Labopol-25 (Struers GmbH) using silicon carbide paper 180-800 (Struers GmbH) at 250 rpm. In further steps the sample is polished using a Rotopol-2 equipped with a Retroforce-4, MD Piano 220 and With a Zeiss Ultra 55 (Carl Zeiss AG), equipped with a field emission electrode, an accelerating voltage of 20 kV is applied, at a pressure of about 3×10–6 mbar. In some cases the cross sections were used to determine the elemental composition along a line across the different layers and perpendicular to the substrate surface. So called line scan was performed using an EDX measurement (energy dispersive X-ray spectroscopy). A IncaPentaFETx3 attached to the Zeiss Ultra 55 and the software "The Microanalysis Suite Issue 18d+SP3" (both from Oxford Instruments) with an aperture of 30 μm were used.

EXAMPLES

One embodiment is now explained in more detail by examples and drawings given by way of example which do not limit it.

Example 1

In this example a FHB is produced from extruded fibres.

Cermet Paste Preparation

A recipe including 1.4 g of cellulose, 10.2 g of de-ionised water, 8.8 g of 99 wt.-% pure alumina and 50.8 g of platinum powder was used to produce the fibres. The preceding ingredients of the recipe were mixed in a high-speed mixer at 1400 rpm.

The thus obtained mixed composition was extruded by a screw extruder having a circular extrusion aperture of diameter 0.78 mm. Therein, the extruded rods arrive on a linear-axis table with adjustable speed. The linear-axis-table is equipped with groove plates. The velocity of the linear-axis table was chosen to be 40 mm/s.

Drilling into Ceramic Green Block

A cubic ceramic green block of alumina was provided. 3 vias were machined into the ceramic green block using a CNC machine at a feed rate of 100 m/min with return stroke. Each via has a diameter of 450 μm.

Filling the Vias

The pre-sintered rods were pressed into the 3 vias of the cubic ceramic green body of alumina. Therein, 1 rod was pressed into each via. The pressing was conducted in a conventional mold (pressing dye) having lateral hole plates. For the selected mould, in which it was possible to place various of the pre-sintered rods in various directions, a force of 6 kN was found to be sufficient, which equals a pressure of about 25 MPa. This maximum pressure was held for 10 s and then released. After the pressing step, a hole was drilled into the green body to come in contact with the rods in the vias of the green body. Again, the CNC machine was used with a feed rate of 100 m/min and return stroke. Said drilled hole was closed by a plug in order to withstand the following cold isostatic pressing (CIP) step. The maximum CIP pressure was chosen to be 2700 bar at room temperature. The plug was removed after the CIP.

Debinding and Firing

Subsequently, a debinding step was conducted. Therein, the temperature was increased to 300° C., then kept constant for 360 min and then decreased to room temperature. Subsequently, the firing of the cubic ceramic body having the rods was conducted. Therein, the temperature was increased to a temperature between 1510° C. to 1600° C., then kept constant for 120 min and then decreased to room temperature. A FHB according to FIG. 1a, however having 3 instead of 1 cermet rod, was obtained.

Afterwards, the hermeticity was assessed by means of a helium leak tester. The working principle is based on helium trespassing the sample and its detection by means of a PHOENIXL 300 mass spectrometer (OC Oerlikon Corporation AG, Pfäffikon, Switzerland). A special sample holder and a flat seal ring are used to mount the specimen vacuum-tight on top of a small chamber. The leak-tight specimen exhibited a leak rate below the detection limit of the machine, which is $10^{-12}$ mbar·L·s$^{-1}$.

Example 2

In this example a FHB was produced by laminating ceramic green sheets.
Paste Recipe 60 g of Pt powder were mixed with 24 g of aluminium oxide powder and a cellulose solvent based organic vehicle and homogenised with a three roll mill. The pastes exhibited a rheology that was suitable for stencil printing.
Ceramic Green Sheet Preparation A ceramic green tape was used as the ceramic green sheet. The ceramic tape used was a 99.7% high purity alumina tape. The green tape thickness was 400 μm. Green tape samples were cut to 90 mm×90 mm squares. About circular holes of 400 μm in diameter were punched into the green tape using a 400 μm diameter mechanical punch in an automatic puncher machine.
Filling The filling of the holes was performed using a stencil with a specific pattern on an EKRA Microtronic II printer (type M2H). The stencil thickness was 100 μm. The stencil openings had the same dimensions and location as the holes punched through the ceramic green tape. The squeegee cycle was set so that cermet material would be deposited in both the forward and backward squeegee movements.

Thereby, a filling of approximately 200 μm thickness after printing (wet), approximately 150 μm thickness after drying was achieved. The filling step was repeated a minimum of 3 times until a satisfactory amount of material was deposited in all holes.
Drying 10 minutes after printing the samples were placed in a drying apparatus and dried at 150° C. for 10 minutes.
Laminating 3 to 7 layers of green tape with the holes filled according to the above process were stacked using a metal aligning tool and isostatically pressed under 350 bar of pressure in an oil bath at elevated temperature in order to achieve the desired component thickness.
Drilling The drilling was optimum, at green state, with a feed rate of 100 mm/min. Return stroke was used. Thereby, a hole contacting the cermet channel through the laminated green sheets as indicated in FIG. 17a was obtained. Said drilled hole was closed by a plug in order to withstand the following processing steps. Therein, the material and dimensions of the plug were chosen to minimize stresses due to the following firing steps and to allow for easy removal after firing.
Firing The resulting laminate of green tapes was fired in a high temperature box oven capable of providing a peak temperature of 1750° C. with a firing chamber of size 200 mm×250 mm×200 mm. The firing took place under normal atmosphere conditions. The temperature was increased to 450° C. in order to burn away organic components remaining in the green laminate. Subsequently, the temperature was increased to a peak temperature in the range from 1510 to 1650° C. and then kept at that temperature for a period of time in the range from 1 to 5 hours. Subsequently, the temperature was decreased to room temperature.
Post-firing Processing After the end of the firing process the plug was removed and the samples were ground and cut to the desired dimensions by laser cutting.

Example 3

In this example a FHB was produced by filling pre-drilled vias of a ceramic green body with a cermet paste.
Drilling into Ceramic Green Block A ceramic green block was provided. A plug hole was machined into the ceramic green block using a CNC machine at a feed rate of 100 m/min with return stroke. Further, 3 vias were machined into the ceramic green block in order to contact the plug hole at different circumferential positions. Each via has a diameter of 450 μm. Again, the CNC machine was used with a feed rate of 100 m/min and return stroke.
Cermet Paste Preparation A recipe including 1.4 g of cellulose, 10.2 g of de-ionised water, 8.8 g of 99 wt.-% pure alumina and 50.8 g of platinum powder was used to produce the fibres. The preceding ingredients of the recipe were mixed in a high-speed mixer at 1400 rpm.
Filling the Vias For each planar surface of the ceramic green block including a via the following was conducted. The ceramic green block was fixed by a holder on a carrier. The vias in the corresponding planar surface of the ceramic green block were filled with the cermet paste using an extrusion via filler Pacific Trinetics (PTC), VF 1'000 which has been modified introducing a vacuum system producing a vacuum from below. The following settings were adjusted taking into account the via diameter of 450 μm and the thickness of the ceramic green block of 6 mm: clamp time=10 s and injection pressure=48 psi. Next, a stainless steel stencil of 5 mils thickness was used. Absorbent paper was placed between the carrier and holder. The cermet paste was injected into the vias at an injection time of 8 seconds and then dried for 1 hour.
Removing Overfills from the Plug Hole Overfills were removed from the plug hole using a small non-metal tip.
Debinding and Firing Subsequently, a debinding step was conducted. Therein, the temperature was increased to 300° C., then kept constant for another 360 min and then decreased to room temperature. Subsequently, the firing of the cubic ceramic body having the rods was conducted. Therein, the temperature was increased to a temperature between 1510° C. to 1600° C., then kept constant for 120 min and then decreased to room temperature.

Final Machining

A final removal of overfills from the plug hole was conducted by drilling.

FIG. 1a illustrates a scheme in perspective of a composite 100 according to one embodiment. The composite includes a ceramic body 101, including a ceramic, which is $Al_2O_3$. The ceramic body 101 is electrically insulating and has a shape of a rectangular box. The ceramic body 101 includes a first surface 102, a hole which is a blind-hole, a second surface 106, and a conductor a1 107. The cylindrically shaped hole includes a front face 103, an end face 104, and a lateral surface 105. The first surface 102 includes the front face 103 as a circular opening in the first surface 102. Thus, the front face 103 is not a material surface of the ceramic body 101. The conductor a1 107 consists of a cermet. The cermet electrically connects the second surface 106 to the lateral surface 105. The conductor a1 105 starts at the second surface 106 and ends at the lateral surface 105. The conductor a1 105 is a straight cylindrical rod made of the cermet. The hole includes an electrically conductive element 108 which is a spring. The composite 100 is a FHB designed for the use in an implantable cardiac pacemaker. Therein, the conductor a1 107 is an electrically conductive feedthrough element which may provide an electrical feedthrough through a hermetically sealed housing of the pacemaker. The hole is designed as a female connector which may accommodate a connector/plug end of a lead of the pacemaker. If the plug end is inserted into the hole, the lead electrically connects to the electrically conductive element 108 which electrically connects to the conductor a1 107. The conductor a1 107 provides an electrical connection to some electronics inside of a housing of the pacemaker. Moreover, the electrically conductive element 108 is a spring which is designed to contribute to fixing the connector end of the lead within the hole. In addition, the lead may be fixed within the hole by means of a screw (not illustrated).

Figure 1B:
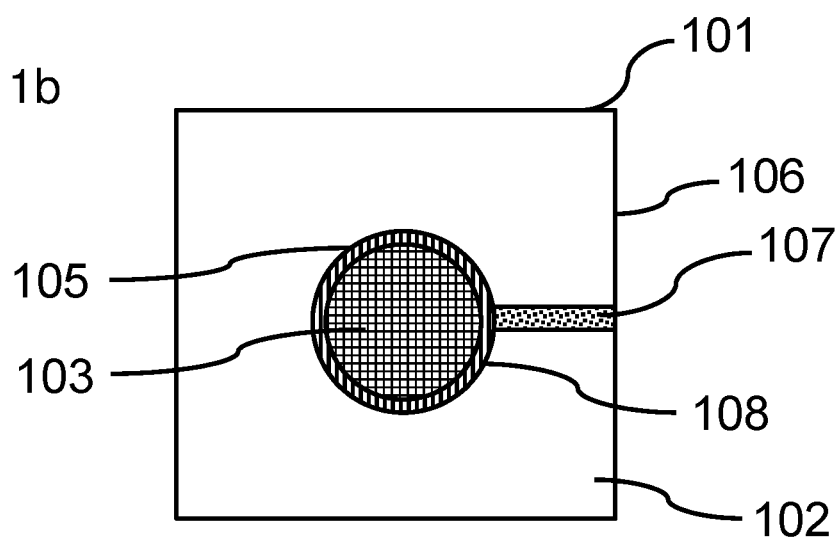

FIG. 1b illustrates a cross-sectional scheme of the composite 100 according to the embodiment of FIG. 1a. The figure illustrates a transversal cross-section through the hole and at the same time a longitudinal cross-section through the conductor a1 107. The first surface 102 is indicated in the figure for orientation, but actually the first surface 102 lies above the plane of the cross-section.

Figure 2A:
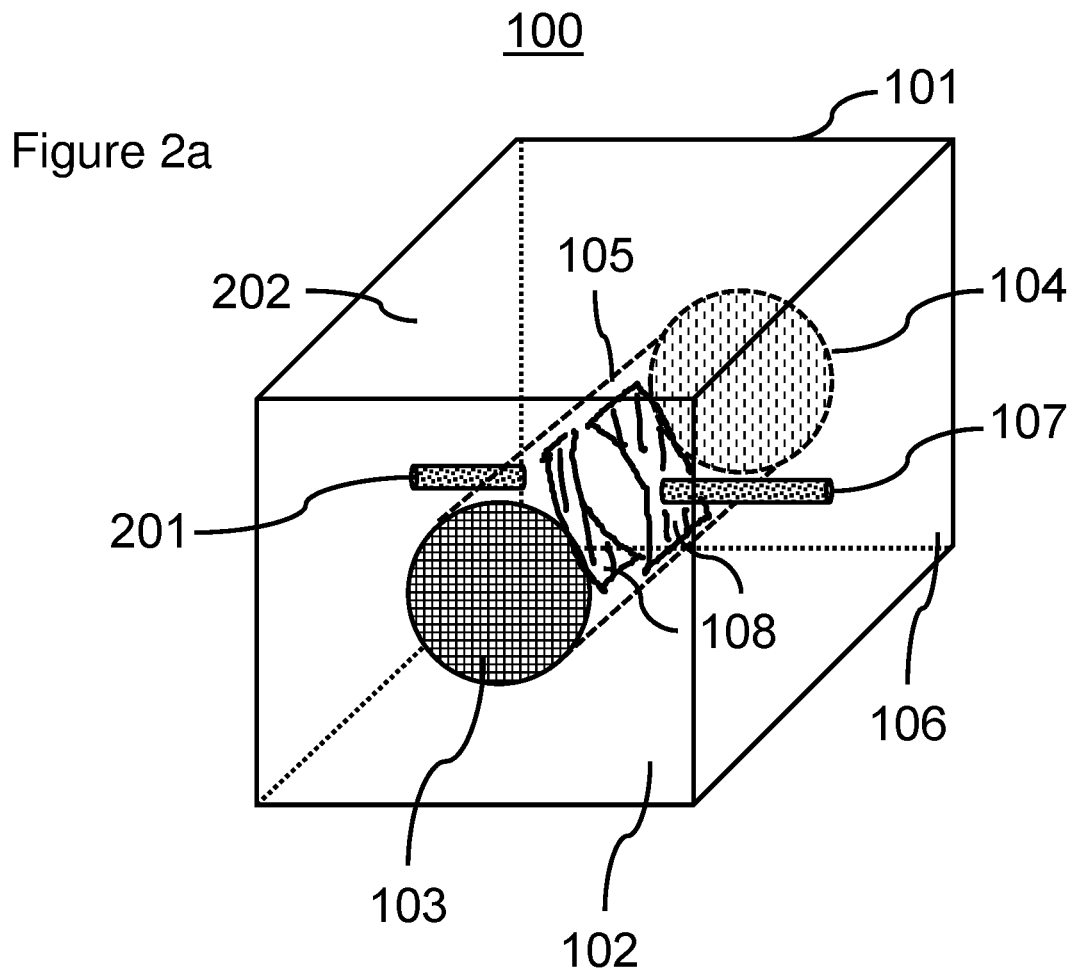
FIG. 2a is a scheme in perspective of another composite according to one embodiment.

FIG. 2a illustrates a scheme in perspective of another composite 100 according to one embodiment. The composite 100 is the same as the composite 100 of FIG. 1a, but the composite 100 of FIG. 2a further includes a further conductor b2 201 which is a straight cylindrical rod made of cermet. The further conductor b2 201 electrically connects a third surface 202 of the ceramic body 101 to the lateral surface 105. Therein, the third surface 202 is opposite to the second surface 106 and adjacent to the first surface 102. The hole includes another electrically conductive element 108 which electrically connects to the further conductor b2 201. Said electrically conductive element 108 is a spring which is separate and electrically insulated from the spring which electrically connects the conductor a1 107. The ceramic body 101 electrically insulates the conductor a1 107 from the further conductor b2 201. Hence, the composite 100 of FIG. 2a provides a 2-polar-FHB. Hence, the composite 100 may electrically connect a 2-polar lead to the electronics of a cardiac pacemaker.

Figure 2B:
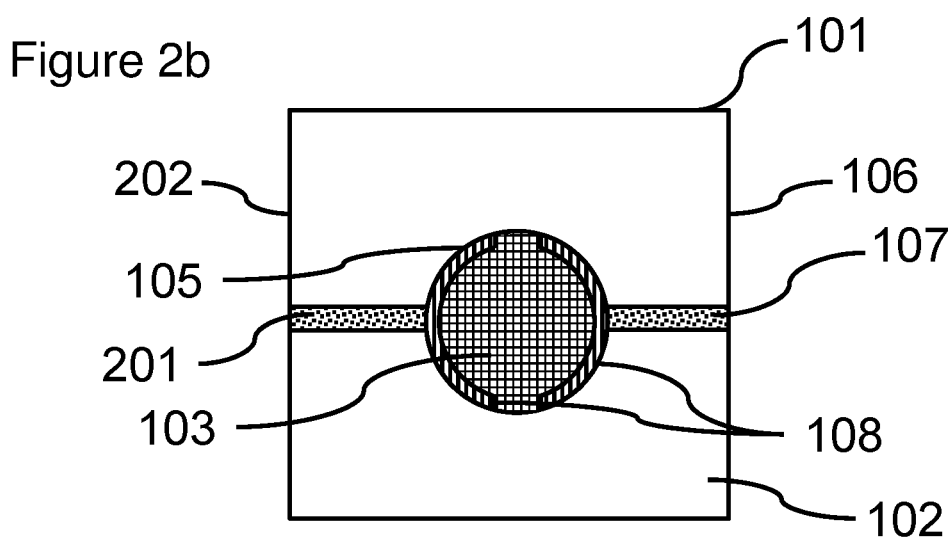

FIG. 2b illustrates a cross-sectional scheme of the composite 100 according to the embodiment of FIG. 2a. The figure illustrates a transversal cross-section through the hole and at the same time a longitudinal cross-section through the conductor a1 107 and the further conductor b2 201. The first surface 102 is indicated in the figure for orientation, but actually the first surface 102 lies above the plane of the cross-section.

FIG. 3a illustrates a scheme in perspective of another composite 100 according to one embodiment. The composite 100 is the same as the composite 100 of FIG. 2a, but the third surface 202 is adjacent to the second surface 202 and adjacent to the first surface 102.

FIG. 3b illustrates a cross-sectional scheme of the composite 100 according to the embodiment of FIG. 3a. The figure illustrates a transversal cross-section through the hole and at the same time a longitudinal cross-section through the conductor a1 107 and the further conductor b2 201. The first surface 102 is indicated in the figure for orientation, but actually the first surface 102 lies above the plane of the cross-section.

Figure 4A:
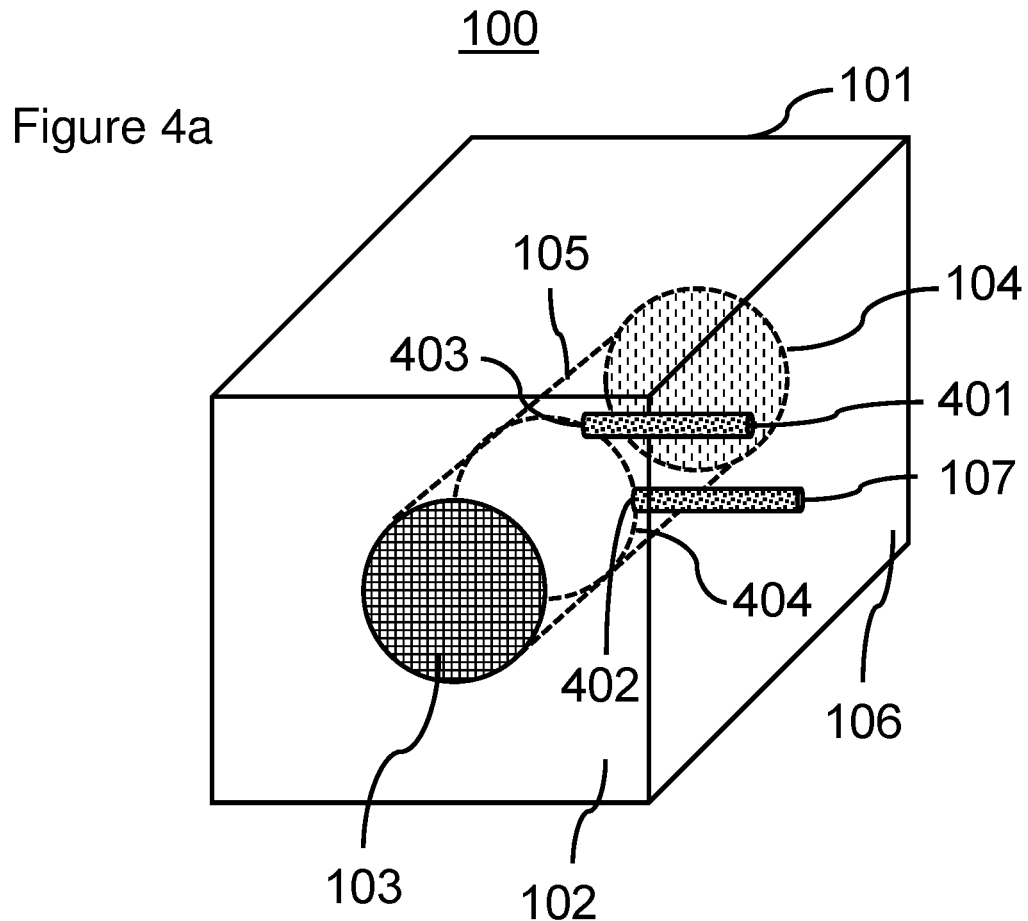
FIG. 4a is a scheme in perspective of another composite according to one embodiment.

FIG. 4a illustrates a scheme in perspective of another composite 100 according to one embodiment. The composite 100 is the same as the composite 100 of FIG. 1a, but the composite 100 of FIG. 4a further includes a further conductor a2 401 which electrically connects the second surface 106 to the lateral surface 105.

The conductor a1 107 connects the second surface 106 to a first circumferential position 402 on the lateral surface 105. The further conductor a2 401 connects the second surface 106 to a further circumferential position 403 on the lateral surface 105. The first circumferential position 402 has a distance from the further circumferential position 403 along a circumference 404 of the lateral surface 105 which is at least $10/360^{th}$ of the circumference 404. This means the first circumferential position 402 is shifted from the further circumferential position 403 along the circumference 404 by at least 10°, under the assumption that the whole circumference 404 extends over 360° around the lateral surface 105. The ceramic body 101 electrically insulates the conductor a1 107 from the further conductor a2 401.

Figure 4B:
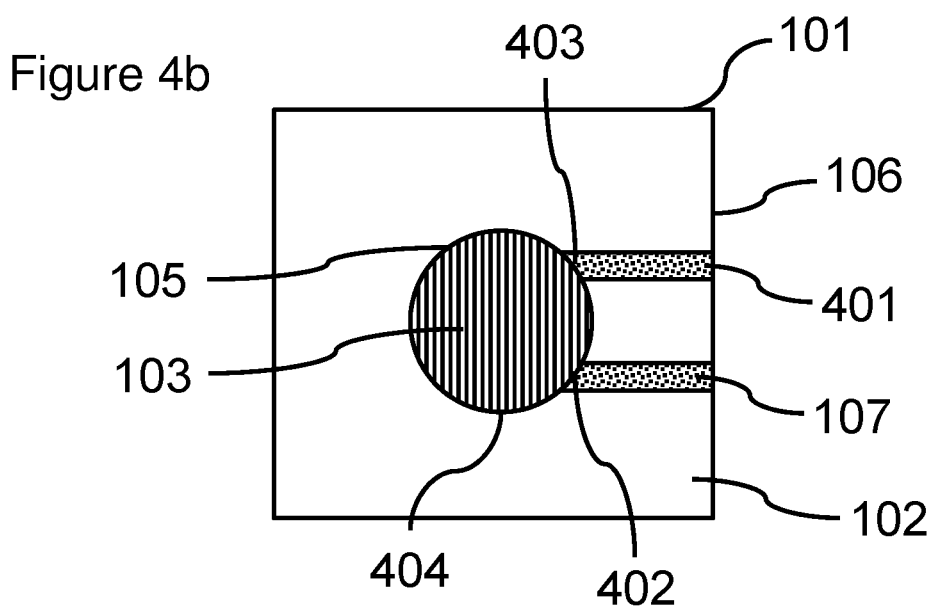

FIG. 4b illustrates a cross-sectional scheme of the composite 100 according to the embodiment of FIG. 4a. The figure illustrates a transversal cross-section through the hole and at the same time a longitudinal cross-section through the conductor a1 107 and the further conductor a2 401. The first surface 102 is indicated in the figure for orientation, but actually the first surface 102 lies above the plane of the cross-section.

Figure 5:
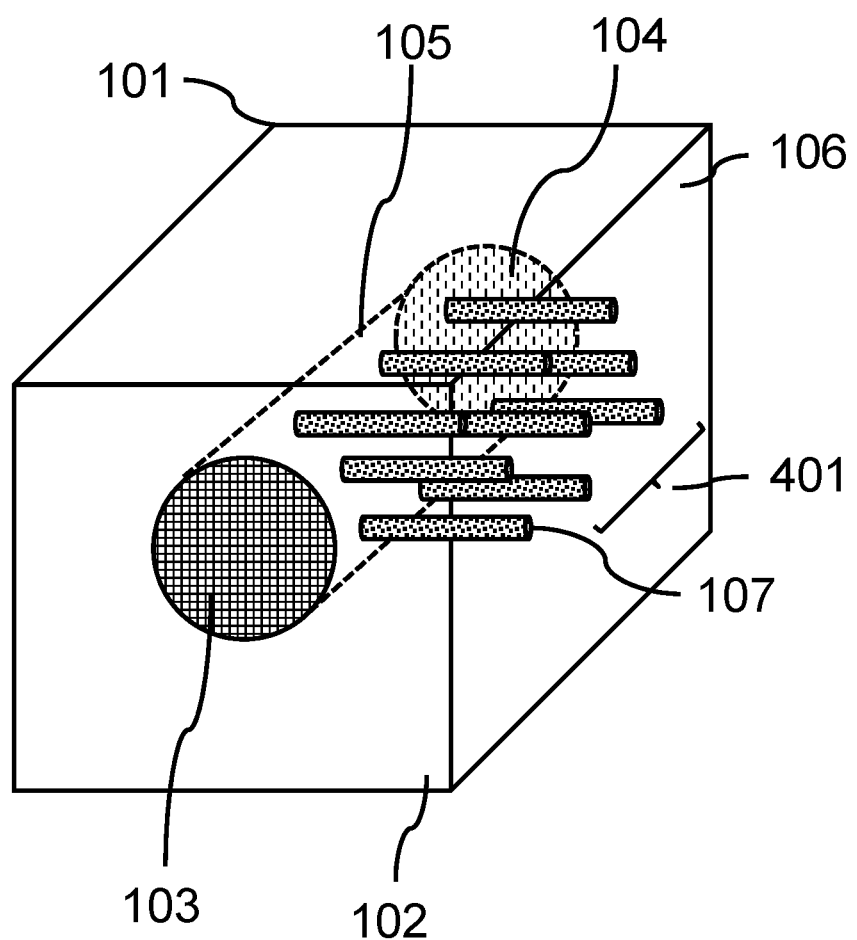
FIG. 5 a scheme in perspective of another composite according to one embodiment.

FIG. 5 illustrates a scheme in perspective of another composite 100 according to one embodiment. The composite 100 is the same as the composite 100 of FIG. 1a, but the composite 100 of FIG. 5 further includes a plurality of further conductors a2 401 which each electrically connect the second surface 106 to the lateral surface 105. The further conductors a2 401 are each made of an electrically conductive cermet. The ceramic body 101 electrically insulates the conductor a1 107 and each further conductor a2 401 from each other. The conductor a1 107 and each further conductor a2 401 are mutually about parallel to each other. The composite 100 of FIG. 5 includes in total 9 conductors 107, 401. Hence, the composite 100 is an FHB which is suitable for electrically connecting a 9-polar lead to an implantable electrical medical device, such as a cardiac pacemaker or an implantable ECG-device.

Figure 6:
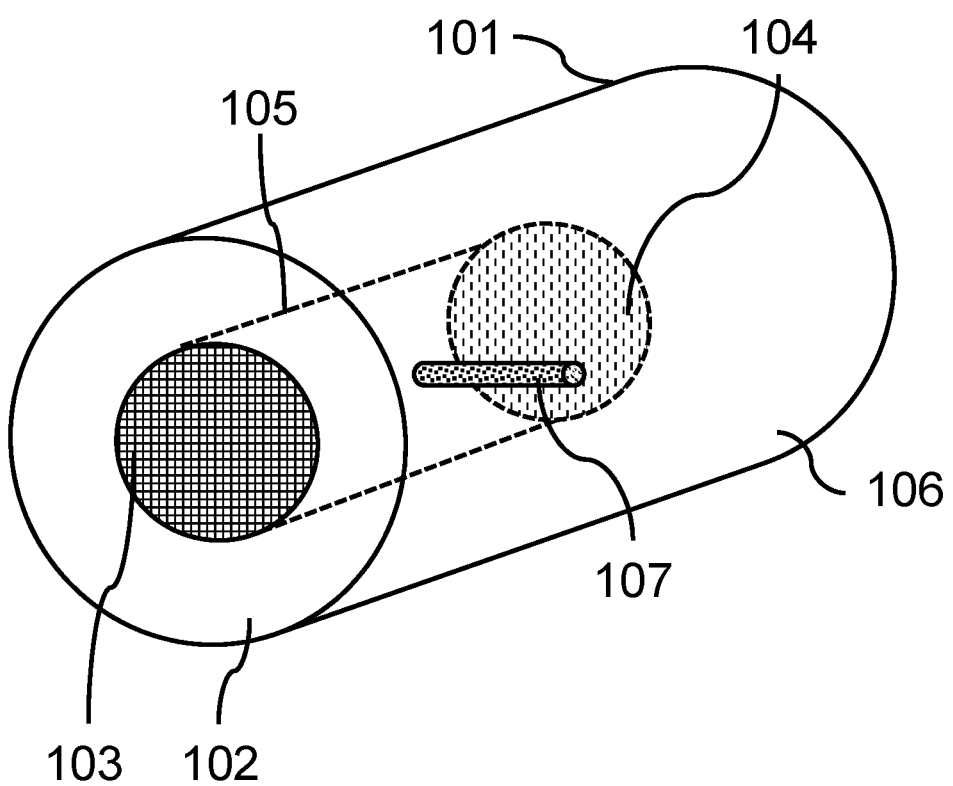
FIG. 6 is a scheme in perspective of another composite according to one embodiment.

FIG. 6 illustrates a scheme in perspective of another composite 100 according to one embodiment. The composite 100 is the same as the composite 100 of FIG. 1a, but the ceramic body 101 of the composite 100 of FIG. 6 is cylindrically shaped. Therein, the first surface 102 is a front face of the cylindrical ceramic body 101. The second surface 106 is a lateral surface of the cylindrical ceramic body 101.

FIG. 6 demonstrates that although most of the other figures illustrate rectangular box-like ceramic bodies 101 of the composites 100 according to one embodiment other shapes are conceivable as well and may even be preferable.

Figure 7:
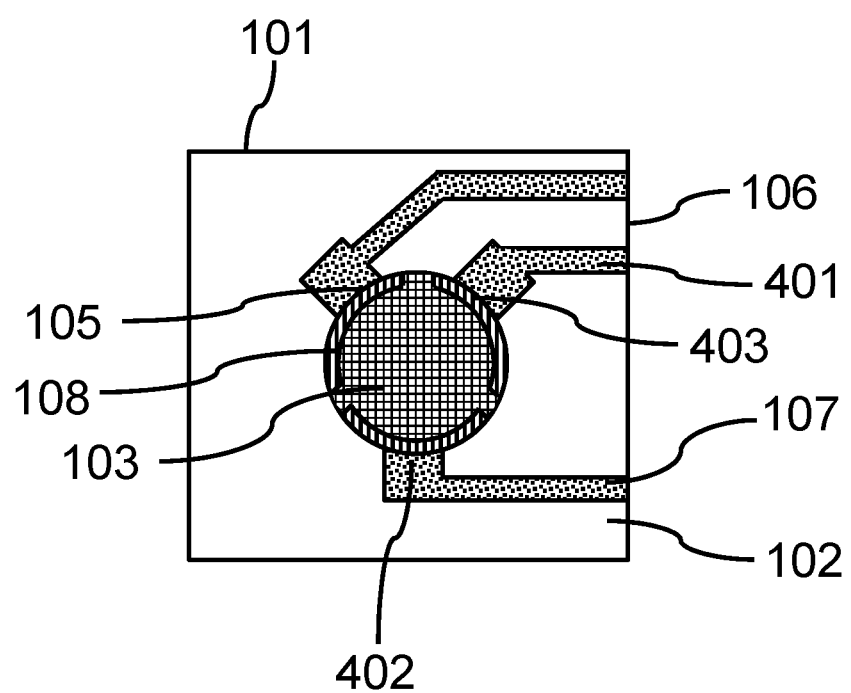
FIG. 7 is a cross-sectional scheme of another composite according to one embodiment.

FIG. 7 illustrates a cross-sectional scheme of another composite 100 according to one embodiment. The composite 100 includes a ceramic body 101 which is rectangular box-like. The ceramic body 101 is made of electrically insulating $Al_2O_3$. The first surface 102 is a sidewall of the rectangular box. The first surface 102 is indicated in the figure for orientation, but actually the first surface 102 lies above the plane of the cross-section. The first surface 102 includes a front face 103 of a cylindrically shaped hole which extends into the ceramic body 101. The front face 103 is an opening in the first surface 102. A lateral surface 105 of the hole connects the front face 103 to an end face 104. As the hole is a blind-hole, the end face 104 lies within the ceramic body 101. Hence, the end face 104 is a material surface of the ceramic body 101. The ceramic body 101 further includes a conductor a1 107 which electrically connects a second surface 106 of the ceramic body 101 to the lateral surface 105 of the hole. The conductor a1 107 is made of an electrically conducting cermet. The conductor a1 107 consists of two straight rod-like pieces which incline an angle. The conductor a1 107 touches the lateral surface 105 at a first circumferential position 402. The ceramic body 101 further includes two further conductors a2 401. Each further conductor a2 401 electrically connects the second surface 106 to a further circumferential position 403 on the lateral surface 105. Each further conductor a2 401 is made of the cermet. Each further conductor a2 401 consists of two straight rod-like pieces which incline an angle. The first circumferential position 402 and the two further circumferential positions 403 are equidistantly distributed over a circumference of the lateral surface 105. Hence, the first circumferential position 402 and the two further circumferential positions 403 are spaced by about 120° along the circumference or by about $\frac{1}{3}^{rd}$ of the circumference. The hole further includes 3 electrically conductive elements 108 which are 3 springs. The 3 springs are separate from each other and not electrically connected to each other. Each spring is electrically connected to exactly one of the conductor a1 107 or the further conductors a2 401. The hole is designed to accommodate a connector/plug end of a lead. Hence, the hole is a female connector. Therein, the springs are designed to electrically connect the plug and hold it in place when the plug has been inserted into the hole. Hence, the composite 100 is a FHB which may electrically connect a 3-polar plug to an implantable electrical medical device, such as a biomonitor or an ECG-device.

Figure 8:
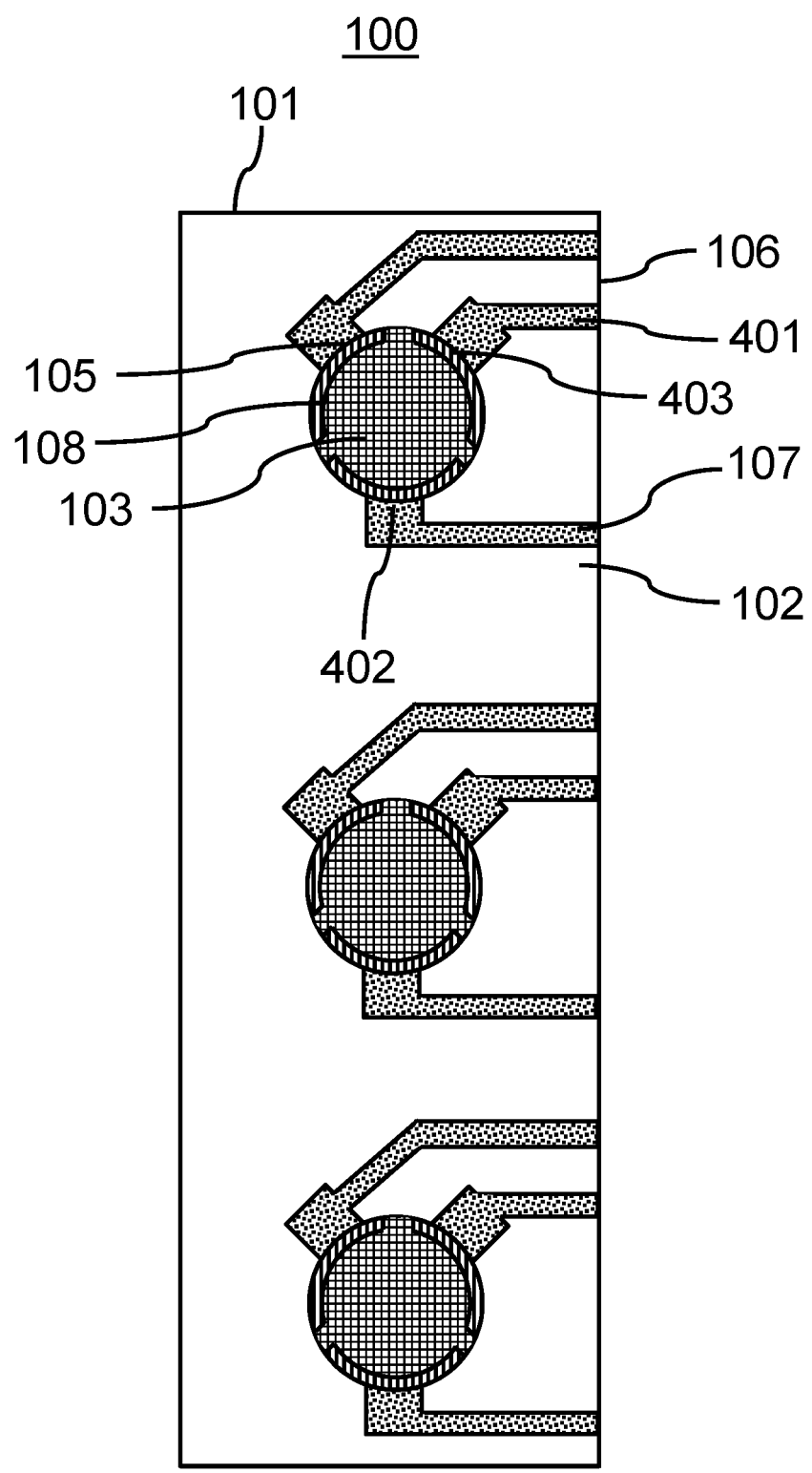
FIG. 8 is a cross-sectional scheme of another composite according to one embodiment.

FIG. 8 illustrates a cross-sectional scheme of another composite 100 according to one embodiment. The composite 100 of FIG. 8 is the same as the composite 100 of FIG. 7, but the ceramic body 101 of FIG. 8 includes 3 holes. Each hole is designed as the hole in FIG. 7. Moreover, each lateral surface 105 is electrically connected to the second surface 106 by a conductor a1 107 and two further conductor a2 401. Therein, the conductors 107, 401 are designed as given in FIG. 7.

Figure 9:
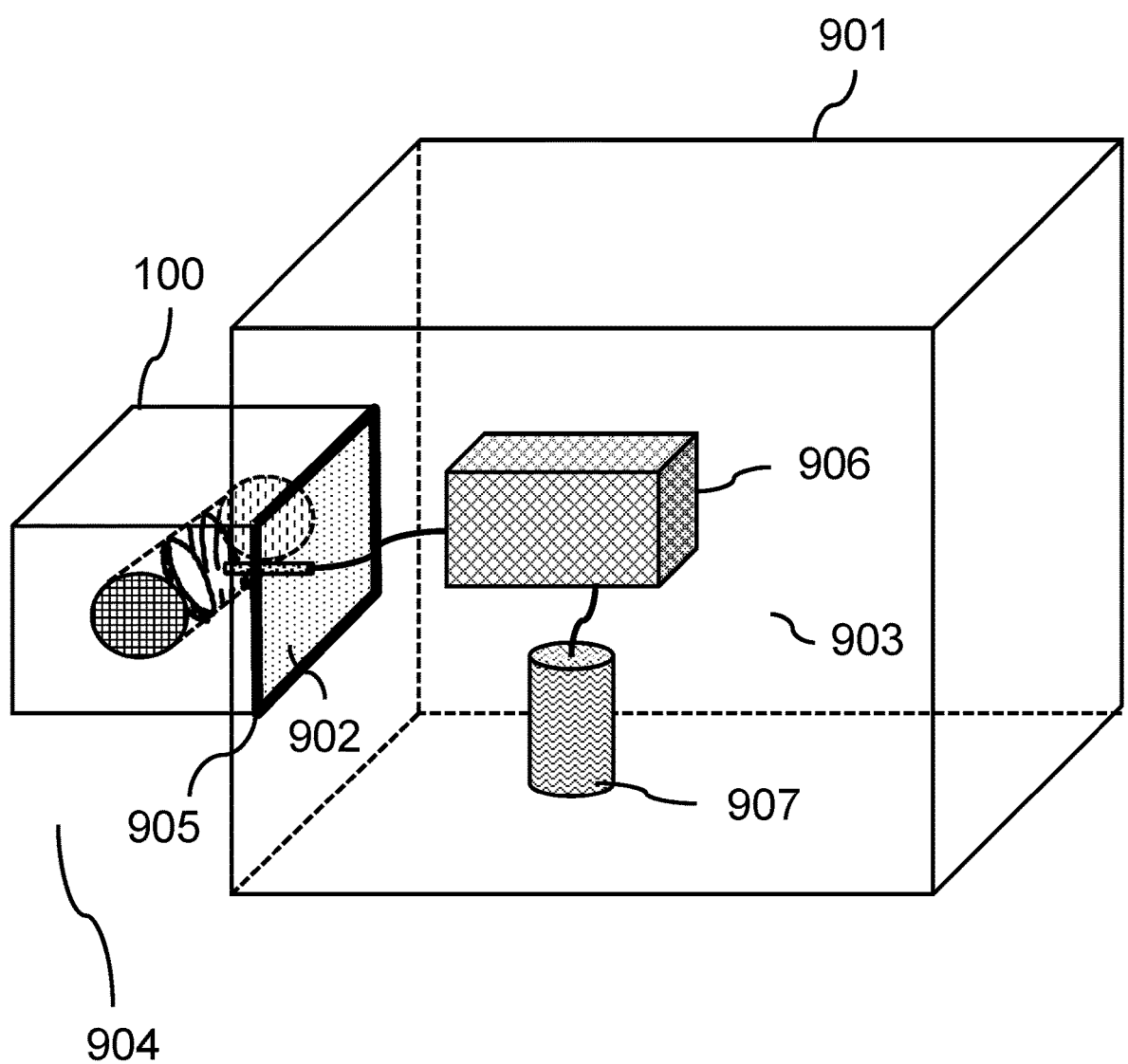
FIG. 9 is a scheme in perspective of a device according to one embodiment.

FIG. 9 illustrates a scheme in perspective of a device 900 according to one embodiment. The device 900 includes a housing 901. The housing 901 is made of a biocompatible material, such as titanium. The housing 901 includes an aperture 902 into which by means of a titanium flange 905 the composite 100 according to FIG. 1a is welded. The composite 100 and the titanium flange 905 hermetically seal the aperture 902. Hence, the housing 901 hermetically seals an inner volume 903, enclosed by the housing 901, from an outer volume 904. Here, the FHB, which is the composite 100, is used in an external arrangement. The hole is outside of the housing 901. Thus, the conductor a1 107 provides a feedthrough element which allows an electrical connection to some electronics 906 and a battery 907 inside the housing 901. The device 900 is an implantable electrical medical device, for example a cardiac pacemaker.

Figure 10:
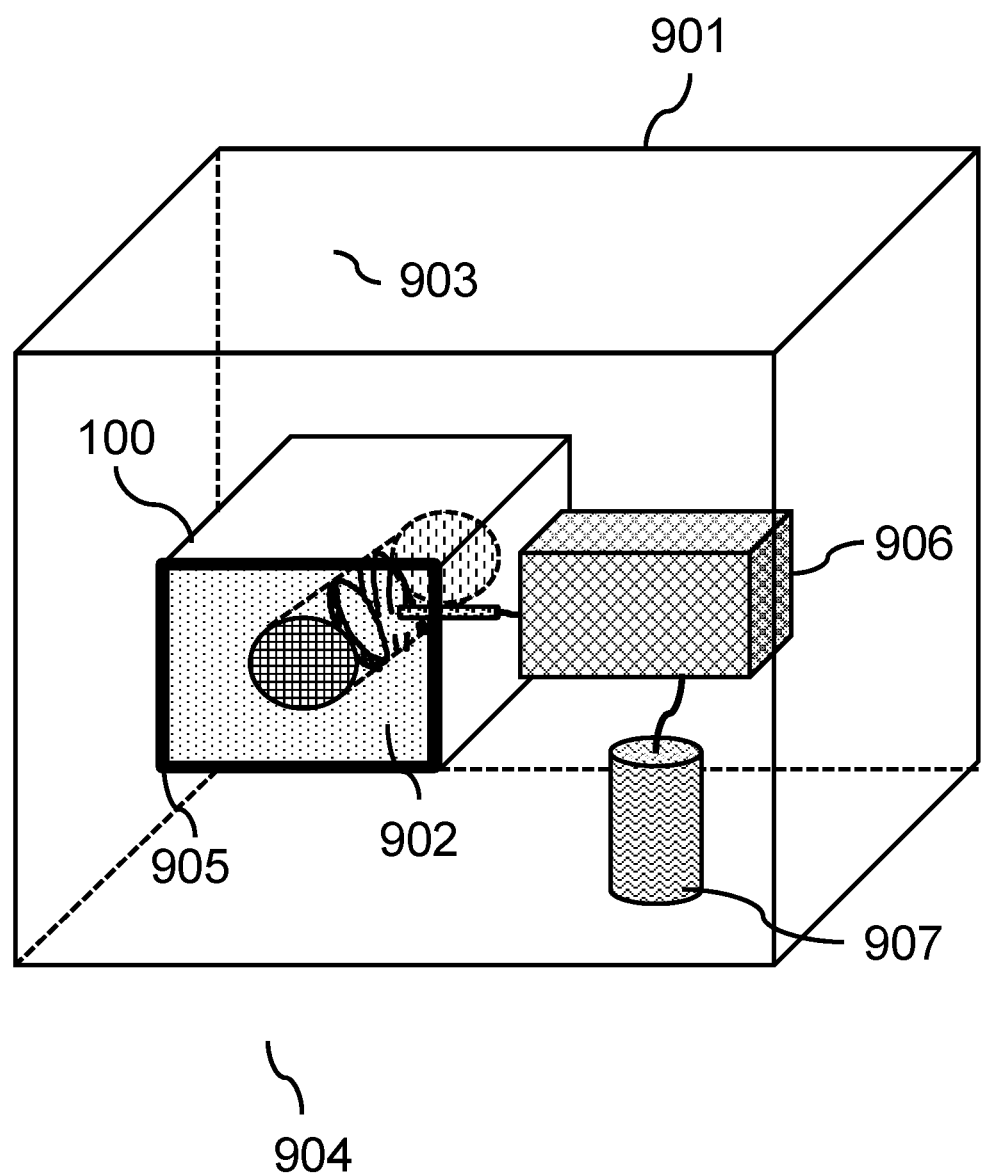
FIG. 10 is a scheme in perspective of another device according to one embodiment.

FIG. 10 illustrates a scheme in perspective of another device 900 according to one embodiment. The device 900 includes a housing 901. The housing 901 is made of a biocompatible material, such as titanium. The housing 901 includes an aperture 902 into which by means of a titanium flange 905 the composite 100 according to FIG. 1a is welded. The composite 100 and the titanium flange 905 hermetically seal the aperture 902. Hence, the housing 901 hermetically seals an inner volume 903, enclosed by the housing 901, from an outer volume 904. Here, the FHB, which is the composite 100, is used in an internal arrangement. The hole is inside the housing 901. The hole and the conductor a1 107 provide an electrical feedthrough which allows an electrical connection to some electronics 906 and a battery 907 inside the housing 901. The device 900 is an implantable electrical medical device, for example a cardiac pacemaker.

Figure 11:
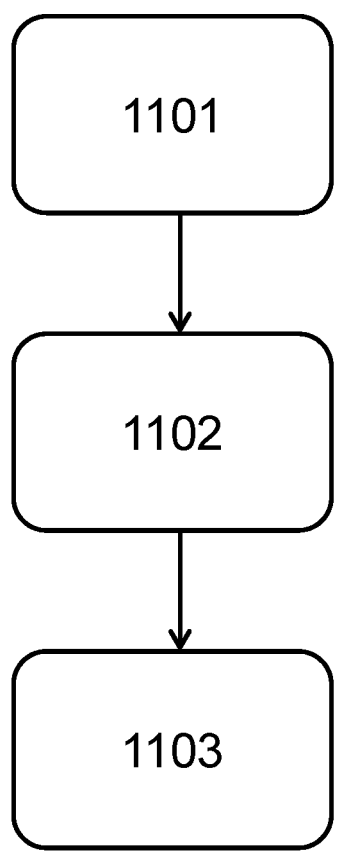
FIG. 11 is a flow chart of another process according to one embodiment.

FIG. 11 illustrates a flow chart of another process 1100 according to one embodiment. The process 1100 includes a process step a) 1101: providing a ceramic green body and a cermet precursor composition. Therein, the cermet precursor composition is a paste, including a cermet powder and an organic vehicle. The ceramic green body includes a plurality of channels, wherein each channel of the plurality of channels is oriented in the ceramic body such that each channel of the plurality of channels can be connected to the other channels of the plurality of channels by providing exactly one hole extending through the ceramic green body. Therein, said hole is an imaginary means utilised to describe the positioning of the channels only. In a process step b) 1102 the channels are filled with the cermet paste such that each channel includes a continuous path of the cermet paste. In a process step c) 1103 the ceramic green body and the cermet precursor composition are fired in a box oven at a peak temperature of 1900° C. which is kept constant for about 4 hours. Thereby, a ceramic body including a plurality of cermet conductors is obtained. In order to produce a FHB according to one embodiment, the previously imaginary hole may be drilled into the ceramic body obtained by the firing. In the process 1100 the ceramic body is obtained from a pre-prepared, for example by pressing a ceramic powder, ceramic green body. The cermet conductors are obtained by firing a cermet precursor composition together with the ceramic green body.

Figure 12:
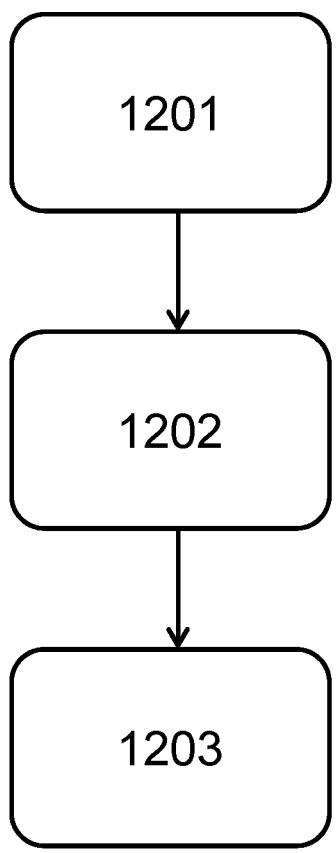
FIG. 12 is a flow chart of another process according to one embodiment.

FIG. 12 illustrates a flow chart of another process 1200 according to one embodiment. The process 1200 includes a process step a) 1201: providing a ceramic green body and a plurality of cermet conductors. Therein, the cermet conductors are cermet rods made of an electrically conductive cermet. The ceramic green body includes a plurality of channels, wherein each channel of the plurality of channels is oriented in the ceramic body such that each channel of the plurality of channels can be connected to the other channels of the plurality of channels by providing exactly one hole extending through the ceramic green body. Therein, said hole is an imaginary means utilised to describe the positioning of the channels only. In a process step b) 1202 one of the cermet conductors is positioned in each of the channels such that in each channel a conducting cermet path is obtained. In a process step c) 1203 the ceramic green body and the cermet conductors are fired in a box oven at a peak temperature of 1600° C. which is kept constant for about 5 hours. Thereby, a ceramic body including the plurality of cermet conductors is obtained. In order to produce a FHB according to one embodiment, the previously imaginary hole may be drilled into the ceramic body obtained by the firing. In the process 1200 the ceramic body is obtained from a pre-prepared, for example by pressing a ceramic powder, ceramic green body.

Figure 13:
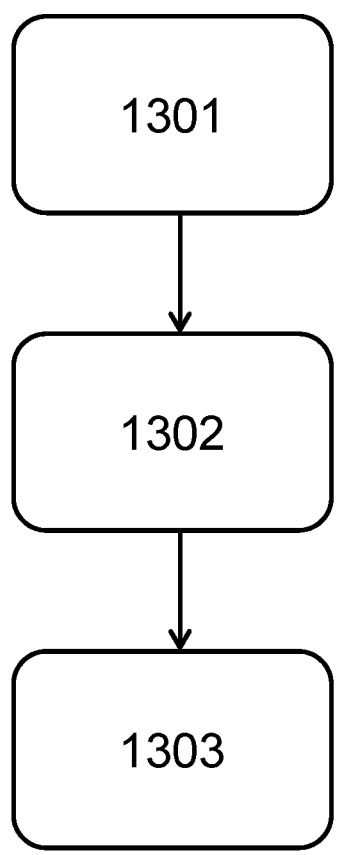
FIG. 13 is a flow chart of another process according to one embodiment.
Figure 14A:
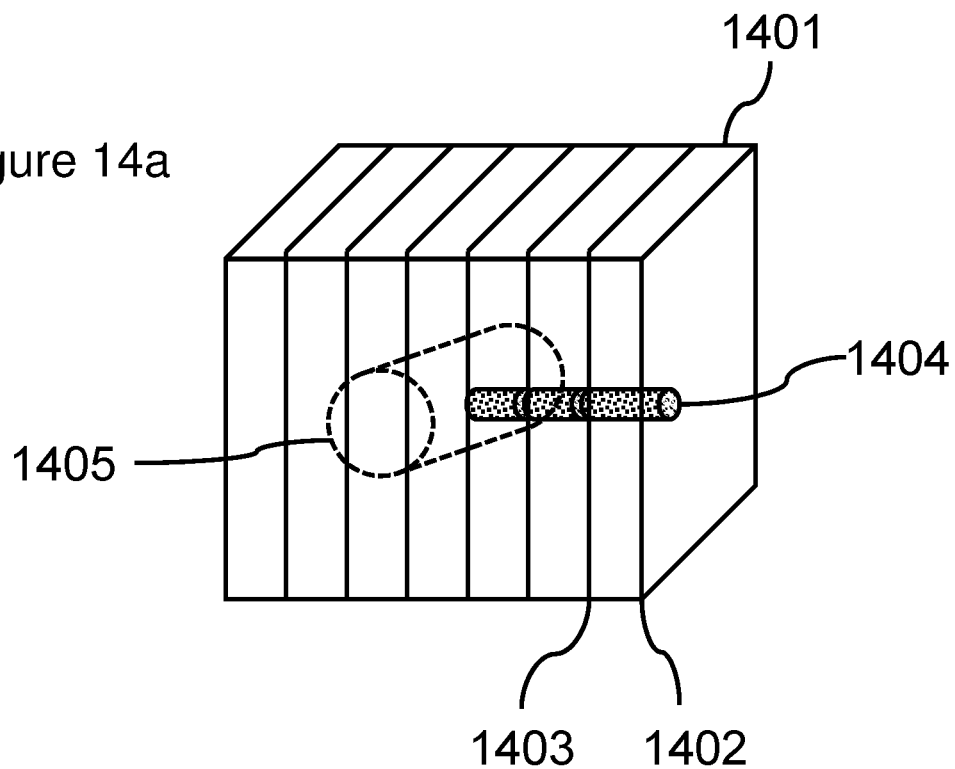
FIG. 14a is a scheme in perspective illustrating the process according to FIG. 13.
Figure 14B:
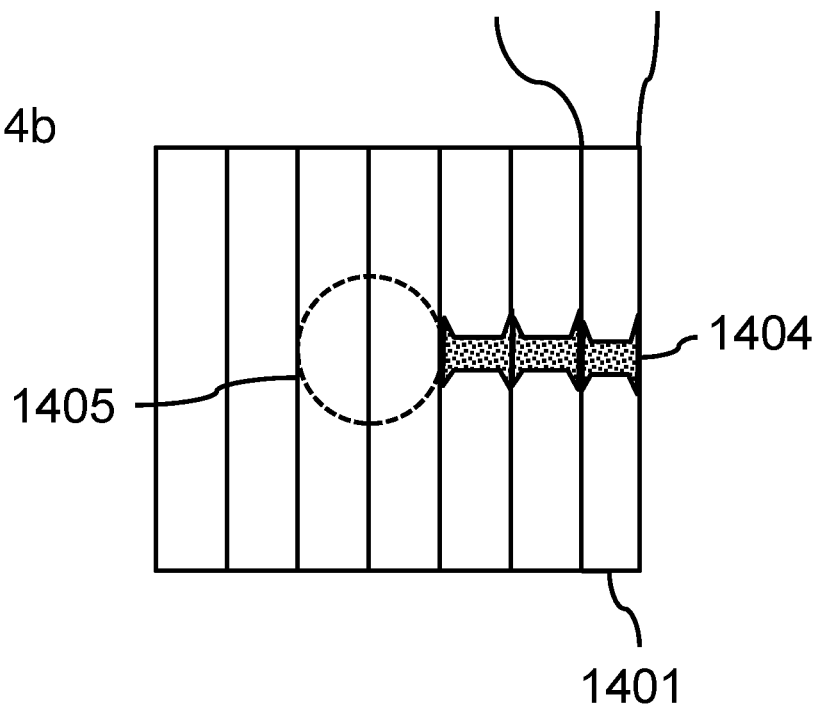

FIG. 13 illustrates a flow chart of another process 1300 according to one embodiment. The process 1300 includes a process step a) 1301: providing a plurality of ceramic green sheets 1401. Each ceramic green sheet 1401 includes a first sheet surface 1402 and a further sheet surface 1403, wherein 3 of the ceramic green sheets each include a first hole 1404, wherein each first hole 1404 connects the first sheet surface 1402 to the further sheet surface 1403 of the corresponding ceramic green sheet 1401. Each first hole 1404 is filled with a quantity of a cermet precursor composition which is a cermet paste. The cermet paste includes 85.5 wt.-% Pt, 4.5 wt.-% $AL_2O_3$ and 10 wt.-% of an organic vehicle, each based on the total weight of the cermet paste. The first holes 1404 are filled with the quantities of the cermet paste by providing one plurality of portions of the cermet paste for each first hole 1404, wherein each plurality of portions of the cermet paste has a first cermet paste volume, wherein each first cermet paste volume is higher than a first hole volume of a corresponding first hole 1404. Next each plurality of portions of the cermet paste has been filled into the corresponding first hole 1404 in subsequent fill-in steps, wherein after each fill-in step a filled in portion of the cermet paste has been dried at 150° C. for 15 minutes. The filling is performed as a printing. Therein, a vacuum is present in the first holes 1404 during the filling. Thereby, each first hole 1404 is overfilled with the cermet paste, which leads to the backbone structure being formed by the cermet paste filled first holes 1404 as illustrated in the FIGS. 14a and 14b. In a process step b) 1302 the first sheet surface 1402 or the further sheet surface 1403 or both of each ceramic green sheet 1401 is laminated to the first sheet surface 1402 or the further sheet surface 1403 of another ceramic green sheet 1401 of the plurality of ceramic green sheets 1401 such that the quantities of the cermet paste in the first holes 1404 form a continuous path of the cermet paste. The laminating is performed by applying a pressure of 350 bar. Hence, the backbone structure of FIGS. 14a and 14b is obtained. In a process step c) 1303 the plurality of ceramic green sheets 1401 and the cermet paste in the first holes 1404 are fired at a peak temperature of 1600° C. which is kept constant for about 5 hours. Thereby, a ceramic body including a cermet conductor is obtained. In order to produce a FHB according to one embodiment after firing a hole is provided in the ceramic body obtained by the firing, wherein the hole includes a front face, an end face and a lateral surface, connecting the front face and the end face, wherein the front face is an opening in the ceramic body, wherein the cermet conductor touches the lateral surface. The process 1300 is further illustrated by the FIGS. 14a and 14b.

FIG. 14a) illustrates a scheme in perspective illustrating the process 1300 according to FIG. 13. For example, the FIG. 14a illustrates the plurality of ceramic green sheets 1401 after laminating them onto each other. The cermet paste which is filled into the 3 first holes 1404 forms a continuous path through the 3 ceramic green sheets 1401 which include the 3 first holes 1404. In FIG. 14a the hole 1405 which may be drilled into the ceramic body after firing is indicated by dashed lines. The hole 1405 is to be designed as a female connector to be suitable for accommodating a male plug end of a lead.

FIG. 14b illustrates a cross-sectional scheme illustrating the same process 1300 as FIG. 14a. For example, FIG. 14b illustrates a cross-section through the plurality of ceramic green sheets 1401 after laminating them onto each other. FIG. 14b indicates the backbone structure formed by the cermet paste in the overfilled first holes 1404. The overfilling is obtained by the filling process described in the context of FIG. 13.

Figure 15A:
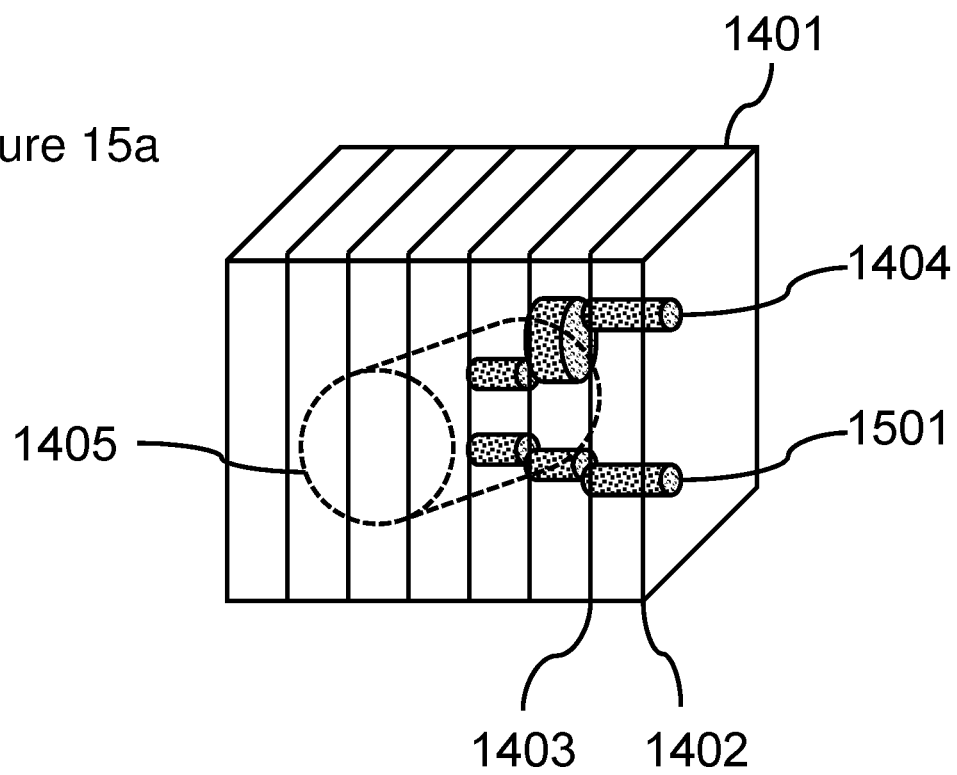
FIG. 15a is a scheme in perspective illustrating another process according to one embodiment.

FIG. 15a illustrates a scheme in perspective illustrating another process 1300 according to one embodiment. The process 1300 is the process 1300 of FIG. 13, except that the 3 ceramic green sheets 1401 which each include a first hole 1404 further each include one further hole 1501. Each further hole 1501 has been filled with the cermet paste in the same way as described in the context of the FIG. 13 for the first holes 1404. By the firing a ceramic body, including 2 cermet conductors is obtained. Moreover, in FIG. 15a the first holes 1404 are positioned non-concentrically next to each other. This way a continuous path of the cermet paste which is not straight but includes linkages is obtained. The same holds for the further holes 1501 and the cermet paste therein.

Figure 15B:
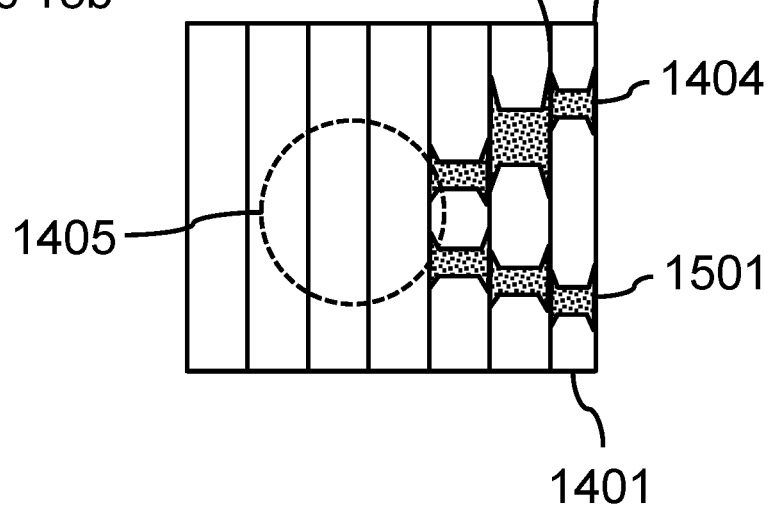

FIG. 15b illustrates a cross-sectional scheme illustrating the same process 1300 as FIG. 15a. For example, FIG. 15b illustrates a cross-section through the plurality of ceramic green sheets 1401 after laminating them onto each other. FIG. 15b indicates the backbone structure formed by the cermet paste in the overfilled first holes 1404 and the overfilled further holes 1501. The overfilling is obtained by the filling process described in the context of FIG. 13.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A composite comprising a ceramic body, comprising:
   a ceramic;
   a first surface;
   a hole, comprising a front face, an end face and a lateral surface, wherein the front face is an opening in the first surface;
   a second surface; and
   a conductor a1;
   wherein the conductor a1 electrically connects the second surface to a first circumferential position on the lateral surface, and comprises a cermet;
   wherein the composite comprises at least one further conductor a2, and wherein each further conductor a2 electrically connects the second surface to the lateral surface, and comprises a cermet;
   wherein at least one further conductor a2 connects the second surface to a second circumferential position on the lateral surface;
   wherein the first circumferential position has a first distance from the second circumferential position along a circumference of the lateral surface; and
   wherein the first distance is at least $1/360^{th}$ of the circumference.

2. The composite of claim 1, wherein the composite comprises a third surface and at least one further conductor b2, wherein each further conductor b2 electrically connects the third surface to the lateral surface, and comprises a cermet.

3. The composite of claim 2,
wherein the at least one further conductor b2 connects the third surface to a third circumferential position on the lateral surface;
wherein the first circumferential position has a further distance from the third circumferential position along a circumference of the lateral surface; and
wherein the further distance is at least $1/360^{th}$ of the circumference.

4. The composite of claim 1, wherein the ceramic body and the conductor a1 are in one piece.

5. The composite of claim 1, wherein the hole accommodates an electrically conductive element.

6. A device comprising a housing, an inner volume, an outer volume, and the composite according to claim 1;
wherein the housing encloses the inner volume, separates the inner volume from the outer volume, and comprises an aperture; and
wherein the aperture frames the composite.

7. The composite of claim 1, arranged in an implantable electrical medical device,
wherein the composite electrically connects the electrode to the implantable electrical medical device.

8. A method comprising:
a) providing a ceramic green body and a cermet precursor composition, wherein the ceramic green body comprises a plurality of channels, wherein each channel of the plurality of channels is oriented in the ceramic body such that each channel of the plurality of channels can be connected to the other channels of the plurality of channels by providing exactly one hole extending through the ceramic green body;
b) filling the channels with the cermet precursor composition; and
c) firing the ceramic green body and the cermet precursor composition, thereby obtaining a ceramic body comprising a plurality of cermet conductors;
wherein the ceramic green body in a) comprises the hole or after c) the hole is provided in the ceramic body, comprising a first surface and a second surface;
wherein the hole comprises a front face, an end face and a lateral surface;
wherein the front face is an opening in the first surface;
wherein each cermet conductor of the plurality of cermet conductors electrically connects the second surface to the lateral surface;
wherein at least one first cermet conductor of the plurality of cermet conductors connects the second surface to a first circumferential position on the lateral surface;
wherein at least one further cermet conductor of the plurality of cermet conductors connects the second surface to a further circumferential position on the lateral surface;
wherein the first circumferential position has a distance from the further circumferential position along a circumference of the lateral surface; and
wherein the first distance is at least $1/360^{th}$ of the circumference.

9. The method of claim 8, wherein the cermet precursor composition is a cermet powder or a cermet paste or both.

10. A method comprising:
a) providing a ceramic green body and a plurality of cermet conductors, wherein the ceramic green body comprises a plurality of channels, wherein each channel of the plurality of channels is oriented in the ceramic body such that each channel of the plurality of channels can be connected to the other channels of the plurality of channels by providing exactly one hole extending through the ceramic green body;
b) positioning one cermet conductor of the plurality of cermet conductors in each channel of the plurality of channels; and
c) firing the ceramic green body and the plurality of cermet conducts, thereby obtaining a ceramic body comprising the plurality of cermet conductors;
wherein the ceramic green body in a) comprises the hole or after c) the hole is provided in the ceramic body, comprising a first surface and a second surface;
wherein the hole comprises a front face, an end face and a lateral surface;
wherein the front face is an opening in the first surface;
wherein each cermet conductor of the plurality of cermet conductors electrically connects the second surface to the lateral surface;
wherein at least one first cermet conductor of the plurality of cermet conductors connects the second surface to a first circumferential position on the lateral surface;
wherein at least one further cermet conductor of the plurality of cermet conductors connects the second surface to a further circumferential position on the lateral surface;
wherein the first circumferential position has a distance from the further circumferential position along a circumference of the lateral surface; and
wherein the first distance is at least $1/360^{th}$ of the circumference.

11. A method comprising:
a) providing a plurality of ceramic green sheets, wherein each ceramic green sheet comprises a first sheet surface and a further sheet surface;
wherein at least two of the ceramic green sheets each comprise a first hole;
wherein the first hole of each of the at least two ceramic green sheets connects the first sheet surface to the further sheet surface of the ceramic green sheet;
wherein each first hole is filled with a quantity of a cermet precursor composition;
b) contacting the first sheet surface or the further sheet surface or both of each ceramic green sheet with the first sheet surface or the further sheet surface of another ceramic green sheet of the plurality of ceramic green sheets such that the quantities of the cermet precursor composition form a continuous path of the cermet precursor composition; and
c) firing the plurality of ceramic green sheets and the cermet precursor composition, thereby obtaining a ceramic body comprising a cermet conductor;
wherein in a) at least two of the ceramic green sheets each comprise n further holes;
wherein each further hole connects the first sheet surface to the further sheet surface of the ceramic green sheet, comprising said further hole;
wherein each further hole is filled with a further quantity of the cermet precursor composition;
wherein in b) the first sheet surface or the further sheet surface or both of each ceramic green sheet is contacted with the first sheet surface or the further sheet surface of another ceramic green sheet of the plurality of ceramic green sheets such that the further quantities of the cermet precursor composition form n continuous paths of the cermet precursor composition;

wherein in c) the ceramic body comprises n further cermet conductors;

wherein n is an integer which is at least 1;

wherein after firing a hole is provided in the ceramic body, wherein the hole comprises a front face, an end face and a lateral surface, connecting the front face to the end face, wherein the front face is an opening in the ceramic body, wherein the cermet conductor and the n further cermet conductors touch the lateral surface;

wherein the cermet conductor connects to a first circumferential position on the lateral surface;

wherein at least one of the n further cermet conductors connects to a further circumferential position on the lateral surface;

wherein the first circumferential position has a distance from the further circumferential position along a circumference of the lateral surface; and wherein the first distance is at least $1/360^{th}$ of the circumference.

12. The method of claim 11, wherein the cermet precursor composition comprises:

Pt in the range from 60 weight % to the remainder completing the sum of all components to 100 weight %;

$Al_2O_3$ in the range from 0.5 to 25 weight %; and a vehicle in the range from 8 to 30 weight %;

each based on the total weight of the cermet precursor composition.

13. A composite obtained by a method comprising:

a) providing a plurality of ceramic green sheets, wherein each ceramic green sheet comprises a first sheet surface and a further sheet surface;

wherein at least two of the ceramic green sheets each comprise a first hole;

wherein the first hole of each of the at least two ceramic green sheets connects the first sheet surface to the further sheet surface of the ceramic green sheet;

wherein each first hole is filled with a quantity of a cermet precursor composition;

b) contacting the first sheet surface or the further sheet surface or both of each ceramic green sheet with the first sheet surface or the further sheet surface of another ceramic green sheet of the plurality of ceramic green sheets such that the quantities of the cermet precursor composition form a continuous path of the cermet precursor composition; and c) firing the plurality of ceramic green sheets and the cermet precursor composition, thereby obtaining a ceramic body comprising a cermet conductor;

wherein in a) at least two of the ceramic green sheets each comprise n further holes;

wherein each further hole connects the first sheet surface to the further sheet surface of the ceramic green sheet, comprising said further hole;

wherein each further hole is filled with a further quantity of the cermet precursor composition;

wherein in b) the first sheet surface or the further sheet surface or both of each ceramic green sheet is contacted with the first sheet surface or the further sheet surface of another ceramic green sheet of the plurality of ceramic green sheets such that the further quantities of the cermet precursor composition form n continuous paths of the cermet precursor composition;

wherein in c) the ceramic body comprises n further cermet conductors;

wherein n is an integer which is at least 1;

wherein after firing a hole is provided in the ceramic body, wherein the hole comprises a front face, an end face and a lateral surface, connecting the front face to the end face, wherein the front face is an opening in the ceramic body, wherein the cermet conductor and the n further cermet conductors touch the lateral surface;

wherein the cermet conductor connects to a first circumferential position on the lateral surface;

wherein at least one of the n further cermet conductors connects to a further circumferential position on the lateral surface;

wherein the first circumferential position has a distance from the further circumferential position along a circumference of the lateral surface; and wherein the first distance is at least $1/360^{th}$ of the circumference.

14. A composite obtained by a method comprising:

a) providing a ceramic green body and a cermet precursor composition, wherein the ceramic green body comprises a plurality of channels, wherein each channel of the plurality of channels is oriented in the ceramic body such that each channel of the plurality of channels can be connected to the other channels of the plurality of channels by providing exactly one hole extending through the ceramic green body;

b) filling the channels with the cermet precursor composition; and c) firing the ceramic green body and the cermet precursor composition, thereby obtaining a ceramic body comprising a plurality of cermet conductors;

wherein the ceramic green body in a) comprises the hole or after c) the hole is provided in the ceramic body, comprising a first surface and a second surface;

wherein the hole comprises a front face, an end face and a lateral surface;

wherein the front face is an opening in the first surface;

wherein each cermet conductor of the plurality of cermet conductors electrically connects the second surface to the lateral surface;

wherein at least one first cermet conductor of the plurality of cermet conductors connects the second surface to a first circumferential position on the lateral surface;

wherein at least one further cermet conductor of the plurality of cermet conductors connects the second surface to a further circumferential position on the lateral surface;

wherein the first circumferential position has a distance from the further circumferential position along a circumference of the lateral surface; and wherein the first distance is at least $1/360^{th}$ of the circumference.

15. A composite obtained by a method comprising:

a) providing a ceramic green body and a plurality of cermet conductors, wherein the ceramic green body comprises a plurality of channels, wherein each channel of the plurality of channels is oriented in the ceramic body such that each channel of the plurality of channels can be connected to the other channels of the plurality of channels by providing exactly one hole extending through the ceramic green body;

b) positioning one cermet conductor of the plurality of cermet conductors in each channel of the plurality of channels; and c) firing the ceramic green body and the plurality of cermet conducts, thereby obtaining a ceramic body comprising the plurality of cermet conductors;

wherein the ceramic green body in a) comprises the hole or after c) the hole is provided in the ceramic body, comprising a first surface and a second surface;

wherein the hole comprises a front face, an end face and a lateral surface;

wherein the front face is an opening in the first surface;

wherein each cermet conductor of the plurality of cermet conductors electrically connects the second surface to the lateral surface;

wherein at least one first cermet conductor of the plurality of cermet conductors connects the second surface to a first circumferential position on the lateral surface;

wherein at least one further cermet conductor of the plurality of cermet conductors connects the second surface to a further circumferential position on the lateral surface;

wherein the first circumferential position has a distance from the further circumferential position along a circumference of the lateral surface; and wherein the first distance is at least $1/360^{th}$ of the circumference.

* * * * *